United States Patent
Lawrence

(10) Patent No.: US 12,150,734 B2
(45) Date of Patent: Nov. 26, 2024

(54) APPARATUS AND A METHOD FOR DETERMINE BIOMETRIC DATA OF A USER AND AN ELECTRONIC DEVICE

(71) Applicant: Intel Corporation, Santa Clara, CA (US)

(72) Inventor: Sean J. W. Lawrence, Bangalore (IN)

(73) Assignee: Intel Corporation, Santa Clara, CA (US)

( * ) Notice: Subject to any disclaimer, the term of this patent is extended or adjusted under 35 U.S.C. 154(b) by 371 days.

(21) Appl. No.: 17/401,355

(22) Filed: Aug. 13, 2021

(65) Prior Publication Data

US 2021/0369117 A1     Dec. 2, 2021

Related U.S. Application Data

(60) Provisional application No. 62/706,399, filed on Aug. 14, 2020.

(51) Int. Cl.
| | |
|---|---|
| *A61B 5/00* | (2006.01) |
| *A61B 5/024* | (2006.01) |
| *A61B 5/103* | (2006.01) |

(52) U.S. Cl.
CPC ........ *A61B 5/0064* (2013.01); *A61B 5/02416* (2013.01); *A61B 5/1034* (2013.01); *A61B 5/6898* (2013.01); *A61B 5/7264* (2013.01); *A61B 5/742* (2013.01); *A61B 2560/0487* (2013.01)

(58) Field of Classification Search
CPC . A61B 5/02416; A61B 5/6898; A61B 5/7264; A61B 2560/0487
See application file for complete search history.

(56) References Cited

U.S. PATENT DOCUMENTS

| | | | |
|---|---|---|---|
| 2015/0173631 A1* | 6/2015 | Richards | A61B 5/7282 600/479 |
| 2020/0133434 A1* | 4/2020 | Lawrence | G06F 3/04166 |

OTHER PUBLICATIONS

Marcus Freitag et al.: "Photoconductivity of biased graphene", https://www.researchgate.net/publication/221666514_Photoconductivity_of_biased_graphene, Feb. 23, 2012.

Dexter Johnson: "Silver Nanowires and Graphene Join Forces for Touch Screen Displays", https://spectrum.ieee.org/nanoclast/semiconductors/materials/graphene-and-silver-nanowires-join-forces-for-touch-screen-displays, Sep. 16, 2016.

Tim Collins et al.: "Some heart-rate monitors give less reliable readings for people of colour", https://theconversation.com/some-heart-rate-monitors-give-less-reliable-readings-for-people-of-colour-121007, Aug. 1, 2019.

(Continued)

*Primary Examiner* — Tammie K Marlen
*Assistant Examiner* — Maria Catherine Anthony
(74) *Attorney, Agent, or Firm* — 2SPL Patent Attorneys PartG mbB; Yong Beom Hwang

(57) ABSTRACT

Particular embodiments described herein provide for an apparatus to determine biometric data of a user including: a processing circuit configured to: generate a control signal relating to a control value for controlling a wavelength of emitted light of a light source; receive biometric input data based on reflected light from the skin of the user caused by the light of the wavelength emitted by the light source; and determine biometric data of the user based on the biometric input data; and an output interface configured to provide the biometric data of the user.

19 Claims, 19 Drawing Sheets

(56) References Cited

OTHER PUBLICATIONS

Andreia Vieira Moco et al.: "Skin inhomogeneity as a source of error in remote PPG-imaging", https://www.ncbi.nlm.nih.gov/pmc/articles/PMC5119611/, Aug. 2, 2016.

* cited by examiner

APPARATUS AND A METHOD FOR DETERMINE BIOMETRIC DATA OF A USER AND AN ELECTRONIC DEVICE

CROSS-REFERENCE TO RELATED APPLICATIONS

This application claims the benefit of U.S. Provisional Application 62/706,399, entitled "Apparatus to Determine Biometric Data of a User," filed Aug. 14, 2020, which is incorporated herein by reference in its entirety.

TECHNICAL FIELD

This disclosure relates in general to the field of computing, and more particularly, to a touchscreen with one or more biosensors.

BACKGROUND

Some emerging trends in electronic devices include the use of a touchscreen. A touchscreen is a both an input device and an output device and is normally layered on the top of an electronic visual display of an information processing system. A user can give input or control the information processing system through simple or multi-touch gestures by touching the screen with a special stylus or one or more fingers. The touchscreen enables the user to interact directly with what is displayed, rather than using a mouse, touchpad, or other such devices (other than a stylus, which is optional for most modern touchscreens). Touchscreens are common in devices such as personal computers, smartphones, personal digital assistance, game consoles, etc.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which.

Figure 1:
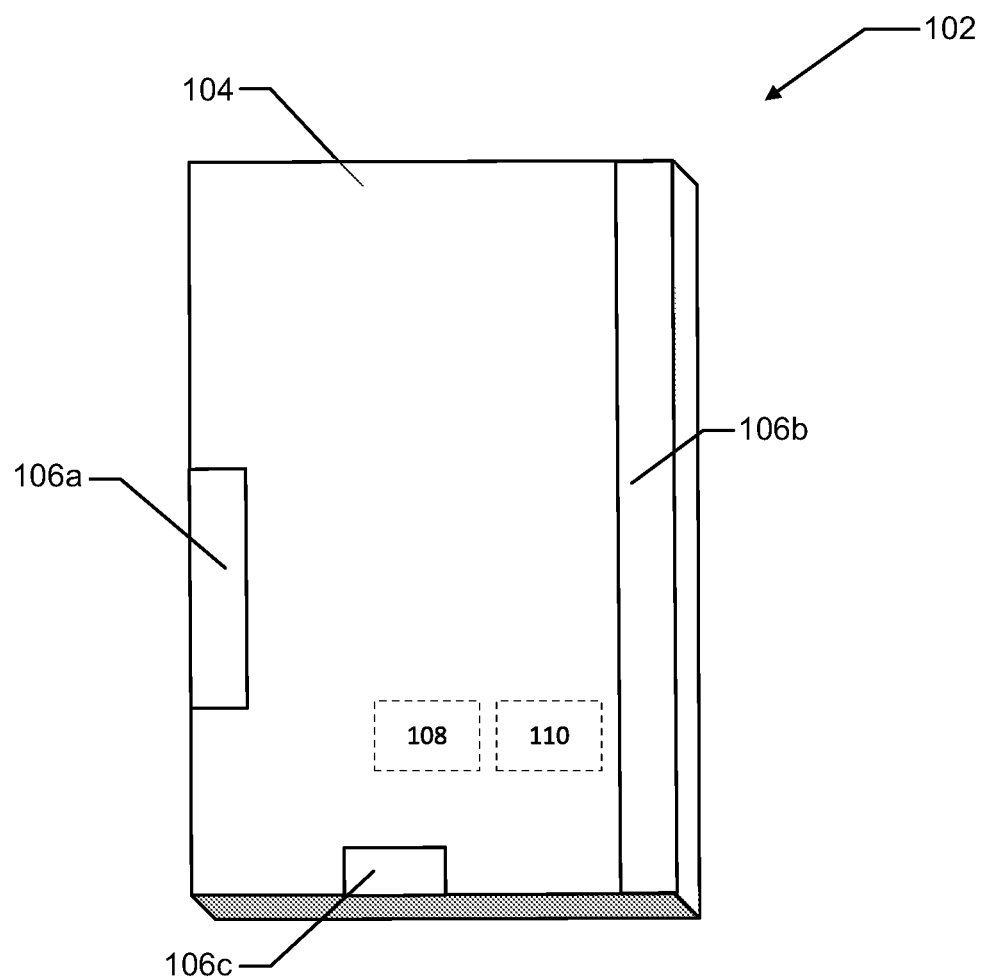
FIG. 1 is a simplified block diagram of a system to enable a touchscreen with one or more biosensors, in accordance with an embodiment of the present disclosure.

The FIGURES of the drawings are not necessarily drawn to scale, as their dimensions can be varied considerably without departing from the scope of the present disclosure.

DETAILED DESCRIPTION

The following detailed description sets forth examples of devices, apparatuses, methods, and systems relating to a touchscreen with one or more biosensors. Features such as structure(s), function(s), and/or characteristic(s), for example, are described with reference to one embodiment as a matter of convenience; various embodiments may be implemented with any suitable one or more of the described features.

In the following description, various aspects of the illustrative implementations will be described using terms commonly employed by those skilled in the art to convey the substance of their work to others skilled in the art. However, it will be apparent to those skilled in the art that the embodiments disclosed herein may be practiced with only some of the described aspects. For purposes of explanation, specific numbers, materials, and configurations are set forth in order to provide a thorough understanding of the illustrative implementations. However, it will be apparent to one skilled in the art that the embodiments disclosed herein may be practiced without the specific details. In other instances, well-known features are omitted or simplified in order not to obscure the illustrative implementations.

The terms "over," "under," "below," "between," and "on" as used herein refer to a relative position of one layer or component with respect to other layers or components. For example, one layer disposed over or under another layer may be directly in contact with the other layer or may have one or more intervening layers. Moreover, one layer disposed between two layers may be directly in contact with the two layers or may have one or more intervening layers. In contrast, a first layer "directly on" a second layer is in direct contact with that second layer. Similarly, unless explicitly stated otherwise, one feature disposed between two features may be in direct contact with the adjacent features or may have one or more intervening layers.

In the following detailed description, reference is made to the accompanying drawings that form a part hereof wherein like numerals designate like parts throughout, and in which is shown, by way of illustration, embodiments that may be practiced. It is to be understood that other embodiments may be utilized and structural or logical changes may be made without departing from the scope of the present disclosure. Therefore, the following detailed description is not to be taken in a limiting sense. For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B, and C). Reference to "one embodiment" or "an embodiment" in the present disclosure means that a particular feature, structure, or characteristic described in connection with the embodiment is included in at least one embodiment. The appearances of the phrase "in one embodiment" or "in an embodiment" are not necessarily all referring to the same embodiment. The appearances of the phrase "for example," "in an example," or "in some examples" are not necessarily all referring to the same example.

FIG. 1 is a simplified block diagram of an electronic device 102 configured to enable a touchscreen with one or more biosensors, in accordance with an embodiment of the present disclosure. In an example, electronic device 102 can include a touchscreen 104, one or more biosensing areas 106a-106c, a touchscreen engine 108, and a biosensor engine 110.

In a general example, touchscreen 104 can be a capacitive touchscreen. Biosensing areas 106a-106c can include a photoconductive material. The term "photoconductive material" includes material that becomes more electrically conductive due to the absorption of electromagnetic radiation such as visible light, ultraviolet light, infrared light, or gamma radiation. Light from a light source under touchscreen 104 can reflect off of a user's finger. The term "finger" includes fingers, thumb, and/or other digits (e.g., toes) of a user. The different amounts of light reflecting off the user's finger will interact with the photoconductive material and/or components of the touchscreen and create a photocurrent that can be analyzed by biosensor engine 110 to create biometric data related to the user. In an example, touchscreen 104 is a capacitive touchscreen and includes drive lines and sense lines. Biosensing areas 106a-106c can include the drive lines, the sense lines, and the photoconductive material. Touchscreen engine 108 can be configured to use the drive lines and sense lines to detect a user's touch on touchscreen 104. Biosensor engine 110 can be configured to use the drive lines and/or sense lines to determine biometrics related to the user when the user touches one or more biosensing areas 106a-106c.

In a specific example, the photoconductive material in touchscreen 104 can include graphene. Electronic device 102 can be configured to use the photoconductive properties of the graphene along with one or more conductors (e.g., drive lines and/or sense lines) as photoplethysmogram (PPG) sensors within touchscreen 104 to help enable electronic device 102 to process a PPG signal for associated biometric analytics and to create biometric data related to the user. For example, by applying a bias between drive lines and/or sense lines, the system can create photoconductive material based photodiodes (e.g., graphene based photodiodes). The measured signal on the touchscreen's drive lines and/or sense lines can be amplified and processed by the biosensor engine 110 to extract the PPG signal.

More specifically, when electronics device 102 is in a touchscreen mode, electronic device 102 can use the touchscreen drive lines and sense lines (e.g., a silver nanowire (AgNW) mesh) to determine where a user touched touchscreen 104. When electronic device 102 is in a biosensing mode, the drive lines and/or sense lines can be converted to PPG sensors using the photoconductive properties of biased graphene-metal junctions in the graphene and processing by biosensor engine 110. The biased drive lines and/or sense lines used in touchscreen 104 will conduct the changes in photocurrent in the photoconductive material (e.g., graphene) due to different amounts of light reflecting off a user's finger due to the varied blood flow within the user's finger. In some examples, a user is directed with on screen content to portions of touchscreen 106 that are to be used as biosensing regions depending on which lines are provided with PPG sensor functionality for intentional PPG sensing. Biosensor engine 110 can be configured to process the changes in current on the drive lines or sense lines due to the amount of light reflected from the user's finger and the current generated due to the conductance of the photoconductive material.

It is to be understood that other embodiments may be utilized and structural changes may be made without departing from the scope of the present disclosure. Substantial flexibility is provided by electronic device 102 in that any suitable arrangements and configuration may be provided without departing from the teachings of the present disclosure.

For purposes of illustrating certain example techniques of electronic device 102, the following foundational information may be viewed as a basis from which the present disclosure may be properly explained. End users have more media and communications choices than ever before. A number of prominent technological trends are currently afoot (e.g., more computing devices, more online video services, more Internet traffic, etc.), and these trends are changing the media delivery landscape. One change is the use of a touchscreen.

A touchscreen is a both an input device and an output device and is normally layered on the top of an electronic visual display of an information processing system. A user can give input or control the information processing system through simple or multi-touch gestures by touching the screen with a special stylus or one or more fingers. The touchscreen enables the user to interact directly with what is displayed, rather than using a mouse, touchpad, or other similar type devices.

A capacitive touchscreen panel consists of an insulator, such as glass, coated with a transparent conductor, such as silver or indium tin oxide (ITO) (however, ITO can cause several environmental problems due to the use of Indium). As the human body is also an electrical conductor, touching the surface of the capacitive touchscreen with a finger results in a distortion of the capacitive touchscreen's electrostatic field, measurable as a change in capacitance. Different technologies may be used to determine the location of the touch from the user's finger and the location of the touch is sent to the controller for processing.

Another technological trend is the use of biometric sensors. Some current devices try to integrate biometric sensors, in particular PPG sensors on various form factors for intentional sensing. A PPG is an optically obtained measurement that can be used to detect blood volume changes in the microvascular bed of tissue. A PPG is often obtained by illuminating the skin and measuring changes in light absorption. With each cardiac cycle, a user's heart pumps blood to the periphery of the user. Even though this pressure pulse is somewhat damped by the time it reaches the skin, the pressure pulse is enough to distend the arteries and arterioles in the subcutaneous tissue. The change in volume of the arteries and arterioles in the subcutaneous tissue caused by the pressure pulse can be detected by illuminating the skin with the light (e.g., from a light-emitting diode (LED)) and then measuring the amount of light reflected from the skin to a photodiode. Because blood flow to the skin can be modulated by multiple other physiological systems, the PPG can also be used to monitor breathing, hypovolemia, and other circulatory conditions.

When light travels through biological tissues it is absorbed by bones, skin pigments and both venous and arterial blood. Because light is more strongly absorbed by blood than the surrounding tissues, the changes in blood flow can be detected by PPG sensors as changes in the intensity of reflected light. The voltage signal detected by PPG sensors is proportional to the quantity of blood flowing through the blood vessels. Even small changes in blood volume can be detected using the PPG sensors, though it cannot be used to quantify an amount of blood. A PPG signal has several components including volumetric changes in arterial blood which is associated with cardiac activity, variations in venous blood volume which modulates the PPG signal, a DC component showing the tissues' optical property and subtle energy changes in the body, etc.

In some current devices, PPG sensors are located on palm rests, key caps, hinges, and the chassis of electronic devices. However, to locate the PPG sensors on palm rests, key caps, hinges, and the chassis of electronic devices, additional hardware, electronics, and other device modifications are required, resulting in additional bill of material (BOM) for the device. Unfortunately, current touchscreens cannot detect the reflected light or to sense the changes in the reflected light.

A device to help mitigate the thermal challenges of a system, as outlined in FIG. 1, can resolve these issues (and others). In an example, an electronic device (e.g., electronic device 102) can be configured to allow for a touchscreen that includes one or more biosensors. More specifically, a conductor (e.g., drive lines and sense lines in a touchscreen) can be located in a photoconductive material (e.g., graphene material). When the conductor is biased with a voltage, any light indecent on the conductor will generate a photocurrent. For example, light reflected from a finger of a user can create a current in the drive lines and sense lines due to the photoconductivity of the photoconductive material and the current can be used to obtain biometric data of the user. In a specific example, the biometric data can be related to PPG data.

For example, PPG can be measured by illuminating the skin and measuring the changes in light absorption. This is typically done by monitoring the perfusion of blood to the dermis and subcutaneous tissue of the skin. A light source (e.g., LED, OLED, etc.) can transmit light through the touchscreen. The light from the light source will pass through the photoconductive material and create a relatively constant current in the drive lines and sense lines. Also, some of the light from the light source will reflect off of a user's finger and the reflected light can pass through the photoconductive material and create a pulsed current in the drive lines and sense lines. The light that is reflected from the user's finger can be pulsed (an AC component) and the pulses can be directly attributable to variation in blood volume in the skin caused by the pressure pulse of the cardiac cycle. The current on the drive lines and sense lines can be analyzed by a biosensor engine (e.g., biosensor engine 110) to determine biometric data related to the user. More specifically, the biosensor engine can receive a signal that will include constant components of light from the light source and reflected pulses of light from the light source. In some examples, the biosensor engine can be configured to remove the constant components and process the variable component as a PPG signal. The biosensor engine can apply a high pass filter to remove the DC component that represents the constant component from the light source and pass higher frequencies that are caused by the reflected light off of the user's finger and represent the biometric signal. Hence, each cardiac cycle is represented by a PPG wave with a crest and trough. This allows for measurement of physiological parameters of the user such as heart rate.

In another example, a light source (e.g., LED, OLED, etc.) can transmit light onto the skin in pluses. The pulses from the light source will pass through the photoconductive material and create a current in the drive lines and sense lines. Also, some of the pulses of light from the light source will reflect off of a user's finger and the reflected light pulses can pass through the photoconductive material and create a current in the drive lines and sense lines. The biosensor engine can receive a signal that will include components of light from the light source and reflected pulses of light from the light source. The biosensor engine can remove the components from the light source and process the variable component from the light reflected off of the user's finger as a biometric signal that can be used to determine biometric data related to the user.

When a finger is placed on a touchscreen that is made up of photoconductive material, drive lines, and sense lines, the light that is transmitted from the light source (e.g., LED, OLED, etc.) passes through the photoconductive material, drive lines, and sense lines. The finger(s) in contact with the screen are illuminated with the light from the light source and part of this light is reflected back towards the touchscreen by the user's finger. The reflected light will create a current in the drive lines and sense lines due to the photoconductivity of the photoconductive material (e.g., graphene-metal junctions). The reflected component will also create a similar current component that includes a variable component that can be extracted and analyzed by the biosensor engine.

The photocurrent generated during a biosensing mode will be negligible (~nA) compared to the drive current (~µA) that is used during a touchscreen mode and hence, in order to sense voltage/current changes that correspond to a PPG signal, the drive lines that are active during times of the touchscreen mode or touch sensing on the touchscreen will need to be disabled. This can be controlled by a touchscreen engine (e.g., touchscreen engine 108), the biosensor engine, an application activating the biosensing mode, a user activating the biosensing mode, or some other means of activating the biosensing mode or switching from the touchscreen mode to the biosensing mode. After the biometric data is collected, the device can exit the biosensing mode, activate the drive lines, and enter into touchscreen mode to detect a user's touch on the touchscreen.

In an example, during the biosensing mode, portions of the touchscreen at the biosensing area are illuminated in pulses. The pulses are used so that the touchscreen area directly above the light source (e.g., LED, OLED, etc.) may be used for sensing PPG. In a specific example, the pulses from the light source may be generated at least at 25 Hz in order to sample a good quality PPG signal. The reflection of the pulses from the user's finger/s are sensed on the drive lines and/or sense lines, amplified if needed, and analyzed by the biosensor engine to derive the PPG.

In the biosensing mode, touchscreen drive lines or sense lines are used to measure reflected light transitions when a finger comes in contact with the biosensor portions (e.g., biosensing areas 106a-106c) of the touchscreen. The signals from multiple drive lines or sense lines are collected, integrated, and may be amplified to create the PPG related data. Any number of portions of the touchscreen can be reserved for biosensing. Additionally, the only limitation to the size of the biosensing area is the size of the touchscreen and the location of the photoconductive material.

When electronic device is in a touchscreen mode, the biosensors are inactive (not sensing) and the touchscreen will operate as a typical touchscreen where timed drive signal pulses are sent along drive lines and the signal on sense lines are measured to detect when a finger is placed on the touchscreen. When electronic device is in a biosensing mode, the biosensors are activated (e.g., to measure PPG), the touch drive pulse circuit will need to be disabled and typical touch functionality will be disabled in order to measure small changes in current due to reflected light changes. PPG may be sensed for wellness, stress or emotion based use cases, sensing and response by associated applications, etc.

In an example implementation, electronic device 102 is meant to encompass a computer, a personal digital assistant (PDA), a laptop or electronic notebook, a cellular telephone, mobile device, personal digital assistants, smartphones, tablets, an IP phone, wearables, Internet-of-things (IoT) device, network elements, or any other device that includes a touchscreen. Electronic device 102 may include any suitable hardware, software, components, modules, or objects that facilitate the operations thereof, as well as suitable interfaces for receiving, transmitting, and/or otherwise communicating data or information in a network environment. This may be inclusive of appropriate algorithms and communication protocols that allow for the effective exchange of data or information. Electronic device 102 may include virtual elements.

In regards to the internal structure associated with electronic device 102, electronic device 102 can include memory elements for storing information to be used in the operations outlined herein. Electronic device 102 may keep information in any suitable memory element (e.g., random access memory (RANI), read-only memory (ROM), erasable programmable ROM (EPROM), electrically erasable programmable ROM (EEPROM), application specific integrated circuit (ASIC), etc.), software, hardware, firmware, or in any other suitable component, device, element, or object where appropriate and based on particular needs. Any of the memory items discussed herein should be construed as being encompassed within the broad term 'memory element.' Moreover, the information being used, tracked, sent, or received in electronic device 102 could be provided in any database, register, queue, table, cache, control list, or other storage structure, all of which can be referenced at any suitable timeframe. Any such storage options may also be included within the broad term 'memory element' as used herein.

In certain example implementations, the functions outlined herein may be implemented by logic encoded in one or more tangible media (e.g., embedded logic provided in an ASIC, digital signal processor (DSP) instructions, software (potentially inclusive of object code and source code) to be executed by a processor or processing circuitry, or other similar machine, etc.), which may be inclusive of non-transitory computer-readable media. In some of these instances, memory elements can store data used for the operations described herein. This includes the memory elements being able to store software, logic, code, or processor instructions that are executed to carry out the activities described herein.

In an example implementation, elements of electronic device 102 may include software modules (e.g., touchscreen engine 108, biosensor engine 110, etc.) to achieve, or to foster, operations as outlined herein. These modules may be suitably combined in any appropriate manner, which may be based on particular configuration and/or provisioning needs. In example embodiments, such operations may be carried out by hardware, implemented externally to these elements, or included in some other network device to achieve the intended functionality. Furthermore, the modules can be implemented as software, hardware, firmware, or any suitable combination thereof. These elements may also include software (or reciprocating software) that can coordinate with other network elements in order to achieve the operations, as outlined herein.

Additionally, electronic device 102 may include one or more processors and/or processing circuitry that can execute software or an algorithm to perform activities as discussed herein. A processor can execute any type of instructions associated with the data to achieve the operations detailed herein. In one example, the processors could transform an element or an article (e.g., data) from one state or thing to another state or thing. In another example, the activities outlined herein may be implemented with fixed logic or programmable logic (e.g., software/computer instructions executed by a processor) and the elements identified herein could be some type of a programmable processor, programmable digital logic (e.g., a field programmable gate array (FPGA), an erasable programmable read-only memory (EPROM), an electrically erasable programmable read-only memory (EEPROM)) or an ASIC that includes digital logic, software, code, electronic instructions, or any suitable combination thereof. Any of the potential processing elements, modules, and machines described herein should be construed as being encompassed within the broad term 'processor.'

For example, the touchscreen engine 108 and/or the biosensor engine 110 may be implemented by the processing circuit of the apparatus for determining biometric data of a user as described below (e.g. as described in connection with FIG. 10A) or may run on the processing circuit of the apparatus for determining biometric data of a user as described below (e.g. as described in connection with FIG. 10A).

Figure 2A:
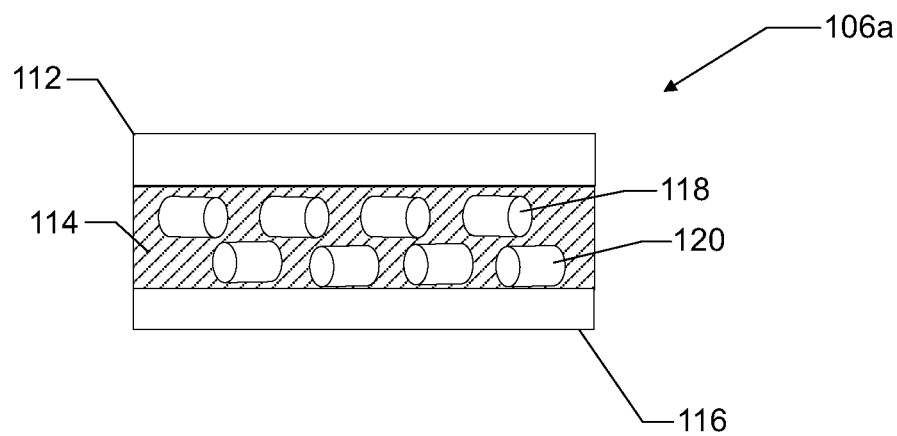
FIG. 2A is a simplified block diagram of a portion of a system to enable a touchscreen with one or more biosensors, in accordance with an embodiment of the present disclosure.

Turning to FIG. 2A, FIG. 2A is a simplified block diagram of a portion of biosensing area 106a. Biosensing area 106a can be configured to operate as a touchscreen area when a biosensing mode is not activated and as a biosensing area when the biosensing mode is activated. Biosensing area 106a can include a protective covering 112, photoconductive material 114, an illumination source 116, drive lines 118, and sense lines 120. Protective covering 112 may be glass or some other protective transparent or semi-transparent material over photoconductive material 114. In an example, illumination source 116 is a plurality of light sources. For example, one or more light sources of the electronic device may be controlled by an apparatus as described in connect with FIG. 10A. In a specific example, illumination source 116 is an array of LED lights or OLED lights. In another example, illumination source 116 is a single light source for touchscreen 104 (illustrated in FIG. 1) where issues with reflection and gradient loss are accounted for by biosensor engine 110. Photoconductive material 114 may be graphene or some other transparent or semi-transparent photo sensitive material that can help enable biosensing area 106a detect biosignals from a user. Drive lines 118 and sense lines 120 are at least partially embedded in or surrounded by photoconductive material 114. Drive lines 118 and sense lines 120 are comprised of a conductive material and are the drive lines and sense lines of touchscreen 104 (illustrated in FIG. 1). In a specific example, drive lines 118 and sense lines 120 are comprised of silver nanowires. When electronic device is in a touchscreen mode, biosensing mode is not activated and a voltage source drives a timed pulse on each of drive lines 118. When a user's finger touches protective covering 112 (e.g., the screen of the electronic device), the current that flows through drive lines 118 changes in capacitance and causes a voltage change in sense lines 120 in the area of the user's finger. The pattern of the voltage changes in sense lines 120 can be analyzed, for example by touchscreen engine 108, to detect where on protective covering 112 the user's finger touched protective covering 112.

Figure 2B:
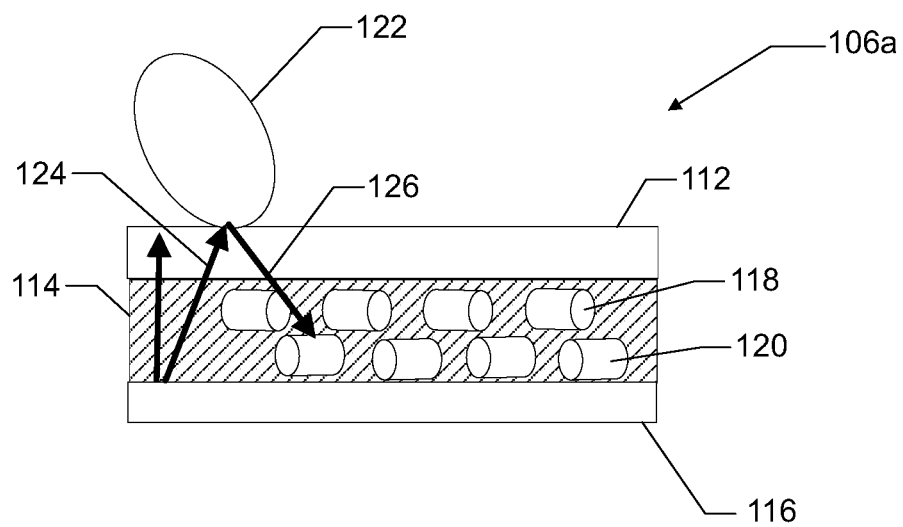
FIG. 2B is a simplified block diagram of a portion of a system to enable a touchscreen with one or more biosensors, in accordance with an embodiment of the present disclosure.

Turning to FIG. 2B, FIG. 2B is a simplified block diagram of a portion of biosensing area 106a. Biosensing area 106a can be configured to operate as a touchscreen area when a biosensing mode is not activated and as a biosensing area when the biosensing mode is activated. Biosensing area 106a can include protective covering 112, photoconductive material 114, illumination source 116, drive lines 118, and sense lines 120.

When the biosensing mode is activated, light 124 from illumination source 116 passes through photoconductive material 114 and protective covering 112. When a user's finger 122 is placed on protective covering 112, a portion of light 124 from illumination source 116 is reflected back towards protective covering 112 and photoconductive material 114 as reflected light 126. Reflected light 126 will pass through protective covering 112 and photoconductive material 114. Reflected light 126 will create a current in drive lines 118 and sense lines 120 due to the photoconductivity of photoconductive material 114. The pattern of the current in drive lines 118 and sense lines 120 due to the photoconductivity of photoconductive material 114 can be analyzed, for example by biosensor engine 110, to determine biometrics of the user. In a specific example, light 124 from illumination source 116 can be generated at least at 25 Hz in order to sample a good quality signal.

Figure 3A:
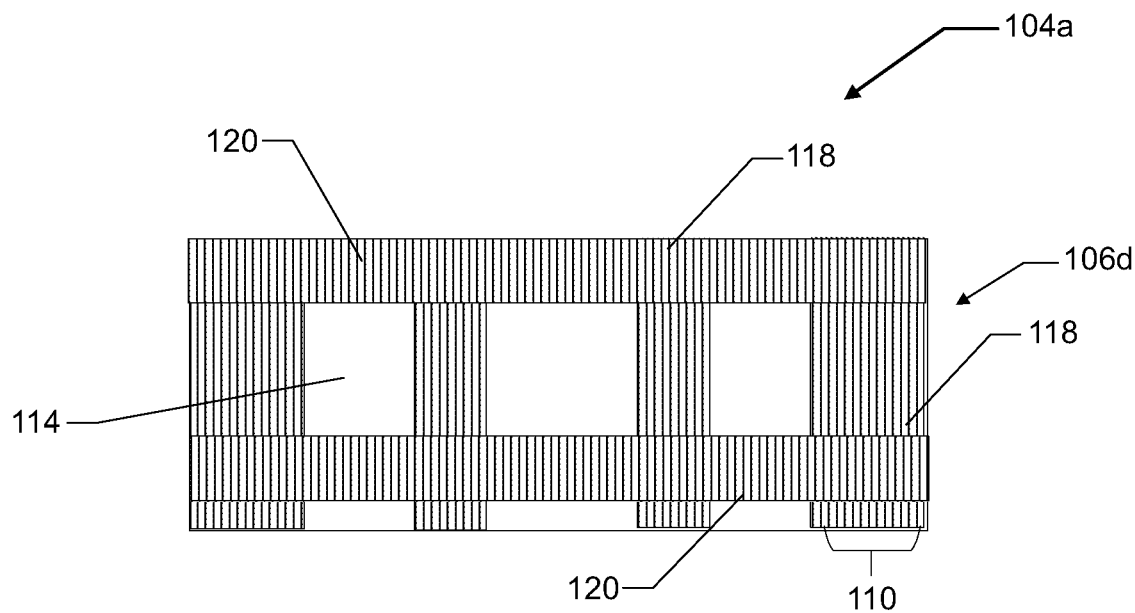
FIG. 3A is a simplified block diagram of a portion of a system to enable a touchscreen with one or more biosensors, in accordance with an embodiment of the present disclosure.

Turning to FIG. 3A, FIG. 3A is a simplified block diagram of a portion of touchscreen 104a. Touchscreen 104a can include biosensing area 106d, drive lines 118, and sense lines 120. In an example, biosensor engine 110 can be coupled to a plurality of drive lines 118 to create biosensing area 106d. The amount of drive lines 118 that are coupled to biosensor engine 110 depends on the strength of the signal or current that can be collected from each individual drive line 118 and design constraints. For example, if the strength of the signal or current that can be collected from each individual drive line 118 is relatively strong, then one or only a few drive lines 118 need to be coupled to biosensor engine 110 or if the strength of the signal or current that can be collected from each individual drive line 118 is relatively very weak, then a large portion or even all of drive lines 118 need to be coupled to biosensor engine 110. As illustration in FIG. 3A, biosensing area 106d is on a side of touchscreen 104a.

Figure 3B:
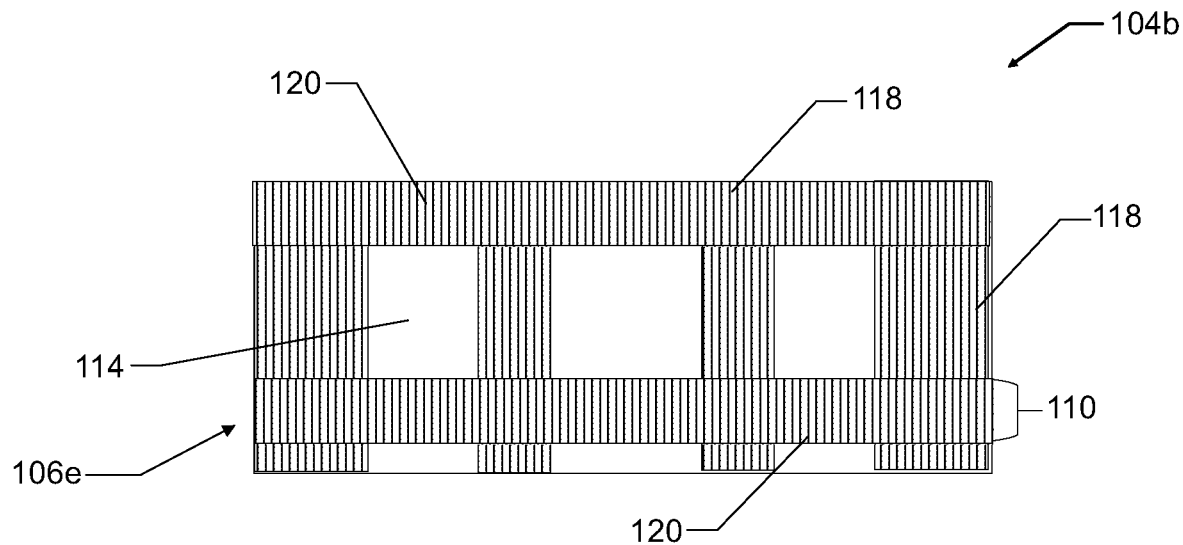
FIG. 3B is a simplified block diagram of a portion of a system to enable a touchscreen with one or more biosensors, in accordance with an embodiment of the present disclosure.

Turning to FIG. 3B, is a simplified block diagram of a portion of touchscreen 104b. Touchscreen 104b can include biosensing area 106e, drive lines 118, and sense lines 120. In an example, biosensor engine 110 can be coupled to a plurality of sense lines 120 to create biosensing area 106e. The amount of sense lines 120 that are coupled to biosensor engine 110 depends on the strength of the signal or current that can be collected from each individual drive line 118 and design constraints. As illustration in FIG. 3B, biosensing area 106e is on a bottom portion of touchscreen 104b.

Figure 3C:
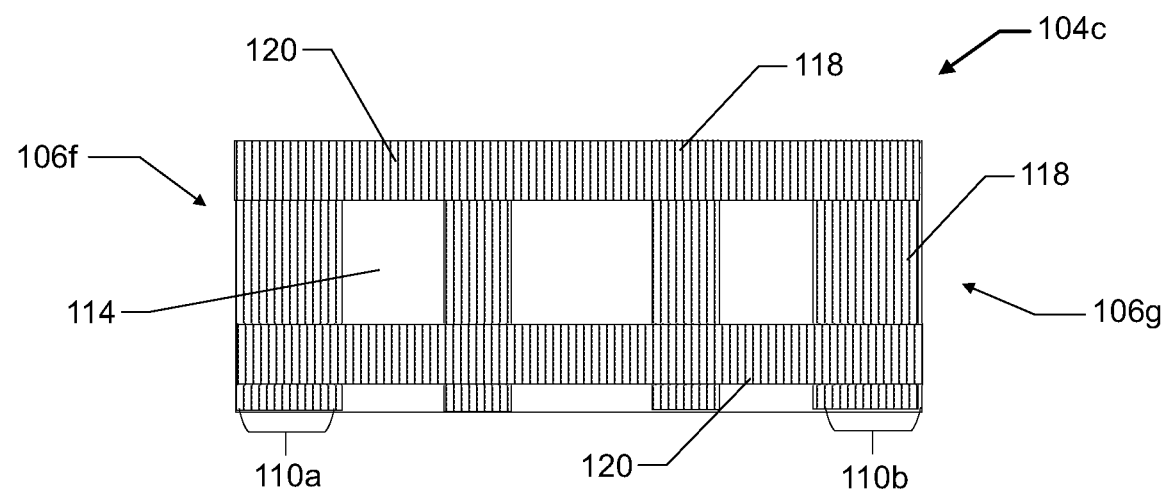
FIG. 3C is a simplified block diagram of a portion of a system to enable a touchscreen with one or more biosensors, in accordance with an embodiment of the present disclosure.

Turning to FIG. 3C, FIG. 3C is a simplified block diagram of a portion of touchscreen 104c. Touchscreen 104c can include biosensing areas 106f and 106g, drive lines 118, and sense lines 120. In an example, biosensor engine 110a can be coupled to a plurality of drive lines 118 to create biosensing area 106f and biosensor engine 110b can be coupled to a plurality of drive lines 118 to create biosensing area 106g. The amount of drive lines 118 that are coupled to biosensor engine 110a and the amount of drive lines 118 that are coupled to biosensor engine 110b depends on the strength of the signal or current that can be collected from each individual drive line 118 and design constraints. As illustration in FIG. 3C, biosensing area 106f is on a first side of touchscreen 104c and biosensing area 106g is on a second side of touchscreen 104c, where the first side of touchscreen 104c is opposite the second side of touchscreen 104c.

Figure 3D:
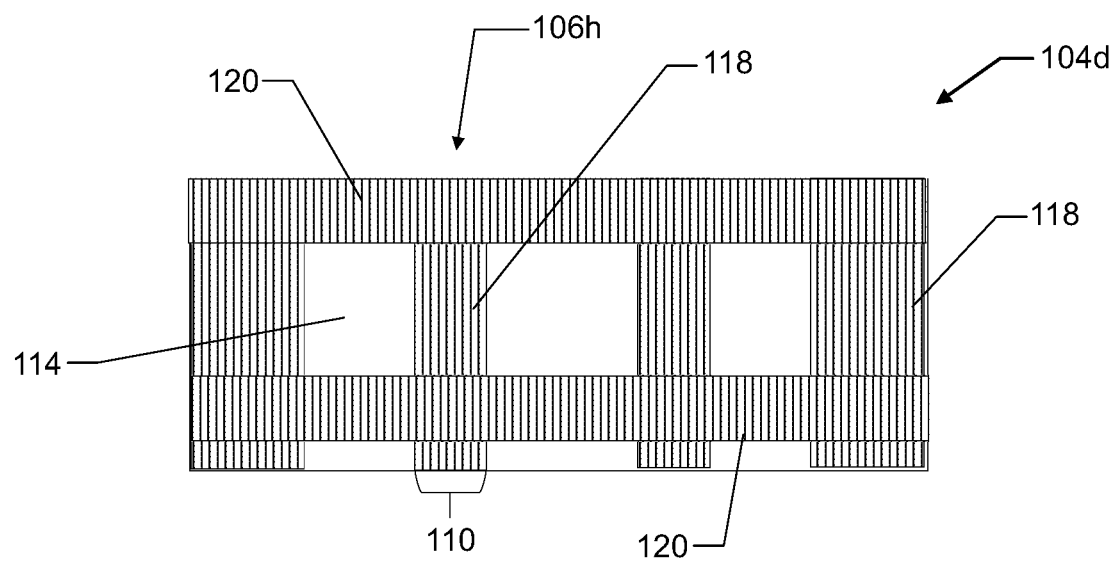
FIG. 3D is a simplified block diagram of a portion of a system to enable a touchscreen with one or more biosensors, in accordance with an embodiment of the present disclosure.

Turning to FIG. 3D, is a simplified block diagram of a portion of touchscreen 104d. Touchscreen 104d can include biosensing area 106h, drive lines 118, and sense lines 120. In an example, biosensor engine 110 can be coupled to a plurality of sense lines 120 to create biosensing area 106h. The amount of sense lines 120 that are coupled to biosensor engine 110 depends on the strength of the signal or current that can be collected from each individual sense line 120 and design constraints. As illustration in FIG. 3D, biosensing area 106f is in a middle portion of touchscreen 104d. It should be noted that the number and location of biosensing areas 106a-106f illustrated in FIGS. 3A-3D are for illustration purposes and the number and location of the biosensing areas can be varied depending on design constraints, user preference, and other factors that will be apparent to one skilled in the art. In a specific example, electronic device 102a and/or touchscreen 104e can display or alert the user to the area where the user should place their finger for biosensing. Biosensor engine 110 can use the area to determine what drive lines 118 or sense lines 120 to use as a biosensing area.

Figure 4A:
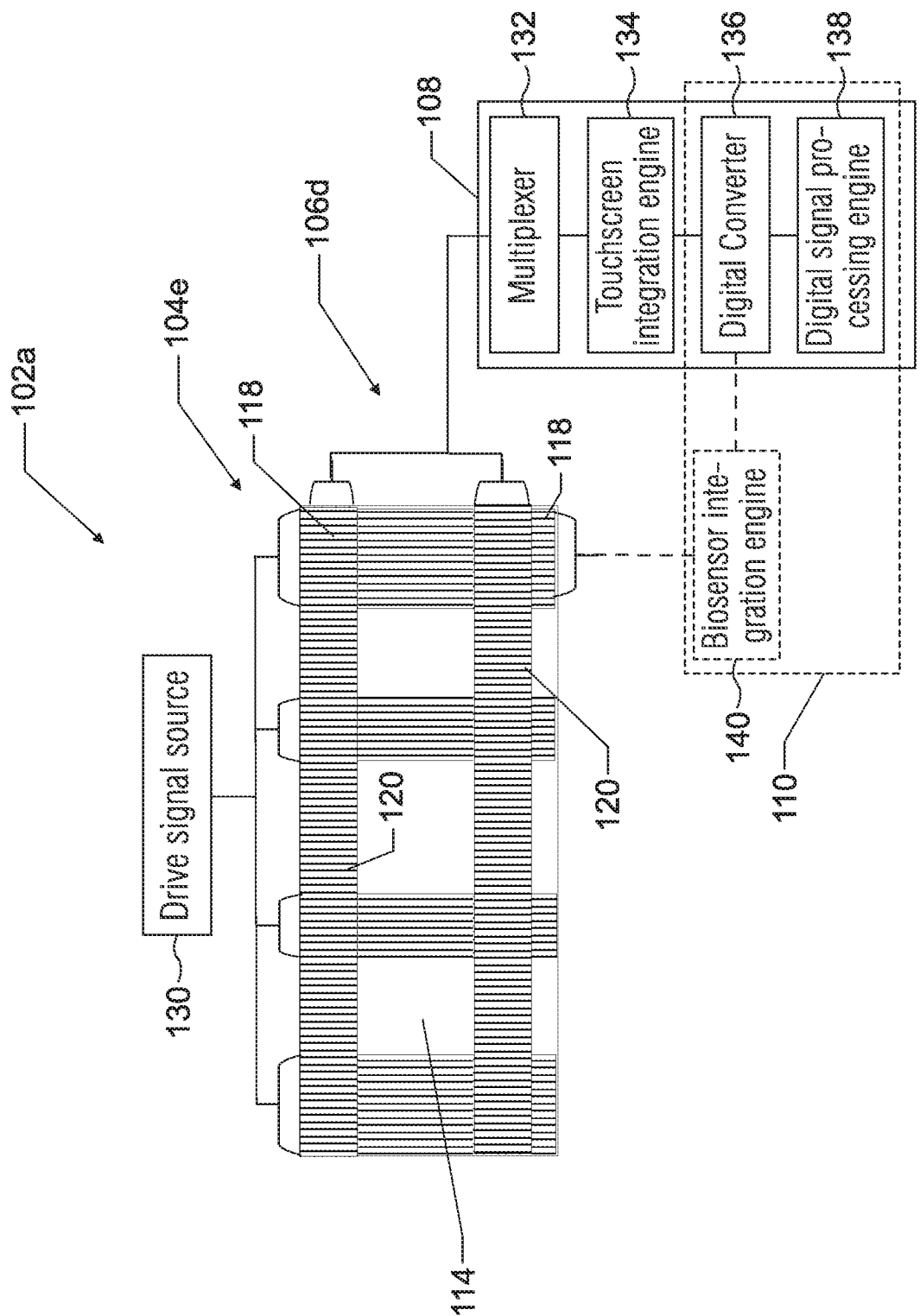
FIG. 4A is a simplified block diagram of a portion of a system to enable a touchscreen with one or more biosensors, in accordance with an embodiment of the present disclosure.

Turning to FIG. 4A, FIG. 4A is a simplified block diagram of a portion of an electronic device 102a when touchscreen mode is enabled. Electronic device 102a can include touchscreen 104e, touchscreen engine 108, biosensor engine 110, and a drive signal source 130. Touchscreen 104e can include photoconductive material 114, drive lines 118, and sense lines 120. Touchscreen engine 108 can include a multiplexer 132, a touchscreen integration engine 134, an analog to digital converter 136, and a digital signal processing engine 138. Biosensor engine 110 can include analog to digital converter 136, digital signal processing engine 138, and a biosensor integration engine 140. Touchscreen 104a can include biosensing area 106d, drive lines 118, and sense lines 120. In an example, biosensor engine 110 can be coupled to a plurality of drive lines 118 to create biosensing area 106d.

Drive signal source 130 can be coupled to drive lines 118 and, when electronic device 102a is in a touchscreen mode, is configured to drive a timed pulse on each of drive lines 118. When a user's finger touches the screen of the electronic device (e.g., protective covering 112), the current that flows through drive line 118 causes a change in capacitance and a voltage change in sense lines 120 in the area of the user's finger. The pattern of the voltage changes in sense lines 120 can be communicated to touchscreen engine 108. The pattern of the voltage changes in sense lines 120 can be analyzed, for example by touchscreen engine 108, to detect where on protective covering 112 the user's finger touched protective covering 112.

More specifically, in an example, the pattern of the voltage changes in sense lines 120 can be communicated to multiplexer 132. Multiplexer 132 multiplexes or combines the output from sense lines 120 and communicates the combined output to touchscreen integration engine 134. Touchscreen integration engine 134 integrates the output of multiplexer 132 with respect to time to create an output (e.g., output voltage) that is proportional to the input from multiplexer 132 (e.g., input voltage) integrated over time. Touchscreen integration engine 134 communicates the integrated output of multiplexer 132 with respect to time to analog to digital converter 136. Analog to digital converter 136 converts the analog output of touchscreen integration engine 134 to a digital signal and communicates the digital signal to digital signal processing engine 138. Digital signal processing engine 138 analyzes the signal from analog to digital converter 136 to detect where on protective covering 112 the user's finger touched protective covering 112.

Figure 4B:
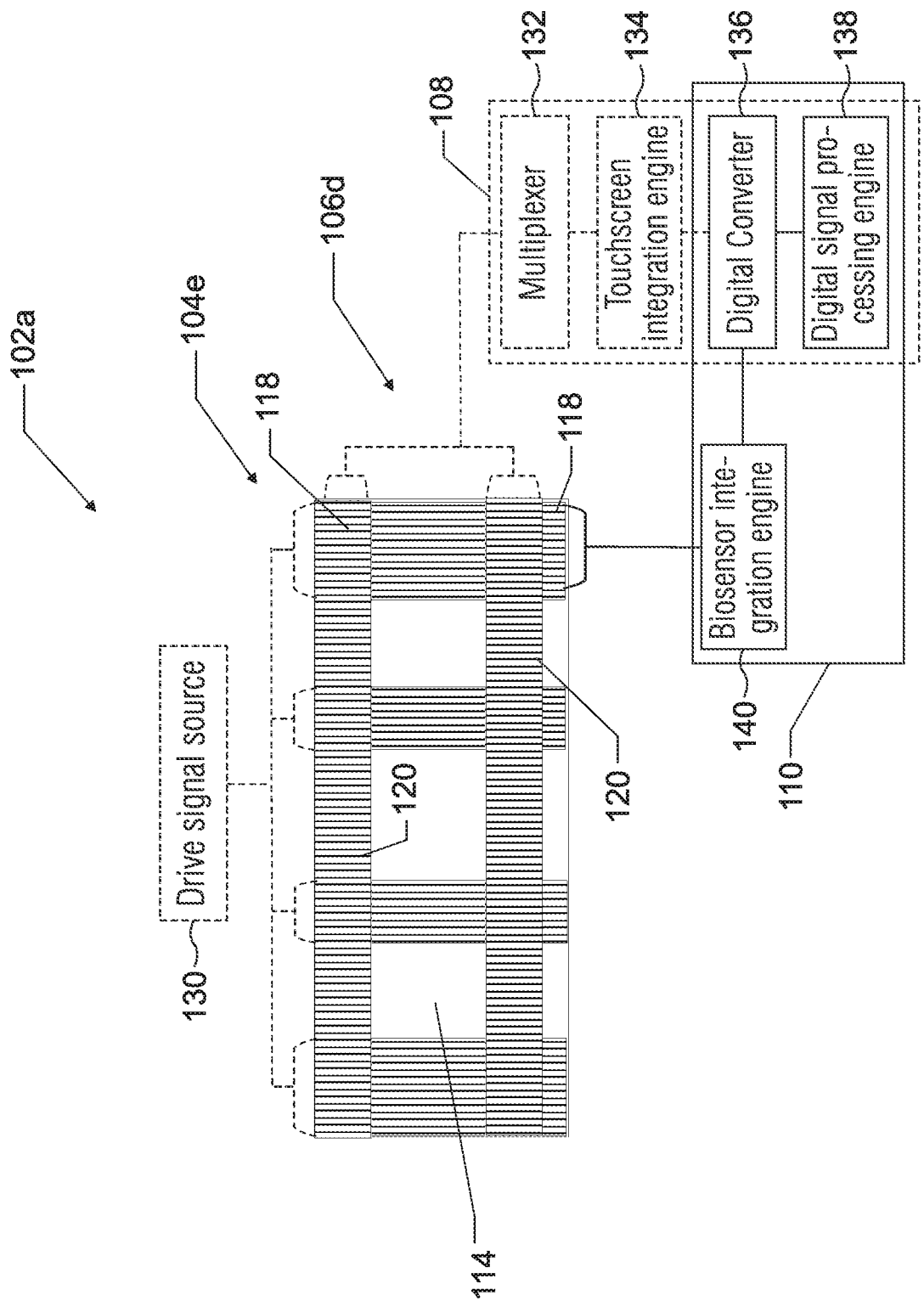
FIG. 4B is a simplified block diagram of a portion of a system to enable a touchscreen with one or more biosensors, in accordance with an embodiment of the present disclosure.

Turning to FIG. 4B, FIG. 4B is a simplified block diagram of a portion of an electronic device 102a when biosensing mode is enabled. Electronic device 102a can include touchscreen 104e, touchscreen engine 108, biosensor engine 110, and drive signal source 130. Touchscreen 104e can include photoconductive material 114, drive lines 118, and sense lines 120. Touchscreen engine 108 can include multiplexer 132, touchscreen integration engine 134, analog to digital converter 136, and digital signal processing engine 138. Biosensor engine 110 can include analog to digital converter 136, digital signal processing engine 138, and biosensor integration engine 140. Touchscreen 104a can include biosensing area 106d, drive lines 118, and sense lines 120. In an example, biosensor engine 110 can be coupled to a plurality of drive lines 118 to create biosensing area 106d.

When a user places their finger in biosensing area 106d, light from a light source (e.g., illumination source 116 illustrated in FIGS. 2A and 2B) under touchscreen 104e can reflect off of the user's finger. The different amounts of light reflecting off the user's finger will interact with photoconductive material 114 and will create a current in drive lines 118 (and sense lines 120) due to the photoconductivity of photoconductive material 114. The current in drive lines 118, due to the photoconductivity of photoconductive material 114, can be analyzed by biosensor engine 110 to create biometric readings of the user.

In an example, the current in drive lines 118 due to the photoconductivity of photoconductive material 114 can be communicated to biosensor integration engine 140. Biosensor integration engine 140 integrates the current in drive lines 118 with respect to time to create an output and communicates the output to analog to digital converter 136. Analog to digital converter 136 converts the analog output of biosensor integration engine 140 to a digital signal and communicates the digital signal to digital signal processing engine 138. Digital signal processing engine 138 analyzes the signal from biosensor integration engine 140 to detect biometric readings of the user.

More specifically, while electronic device 102a is in biosensing mode, the light from the light source (e.g., illumination source 116 illustrated in FIGS. 2A and 2B) will pass through photoconductive material 114 and create a current in drive lines 118 and sense lines 120. Also, some of the light from the light source will reflect off of a user's finger (e.g., user's finger 122 illustrated in FIG. 2B) and the reflected light pulses can pass through photoconductive material 114 and create a current in the drive lines 118 and sense lines 120. The light that is reflected from the user's finger (an AC component) is directly attributable to variation in blood volume in the skin caused by the pressure pulse of the cardiac cycle. The current on one or more of drive line 118 can be collected and integrated by biosensor integration engine 140. Analog to digital converter 136 converts the analog output of biosensor integration engine 140 to a digital signal and communicates the digital signal to digital signal processing engine 138. Digital signal processing engine 138 analyzes the signal from biosensor integration engine 140 that will include constant components of light from the light source and reflected pulses of light from the user's finger. The reflected light from the user's finger will contain the variable current due to the variation in blood volume in the skin caused by the pressure pulse of the cardiac cycle. As a result, each cardiac cycle is represented by a PPG wave with a crest and trough. This allows measurement of physiological parameters such as heart rate.

The light that passes through photoconductive material 114 and creates a current in drive lines 118 and sense lines 120 has a constant component as well as a variable AC component. The constant component is a result due to the incident light from the light source and in some examples, biosensor engine 110 can be configured to remove the constant components and process the variable AC component as the PPG signal. Biosensor integration engine 140 can apply a high pass filter to remove the constant component that represents the light from the light source and pass higher frequencies that are caused by the reflected light off of the user's finer and represent the PPG signal. In some examples, the high pass filter is located before biosensor integration engine 140 receives the signal from drive lines 118 (or sense lines 120).

Figure 5A:
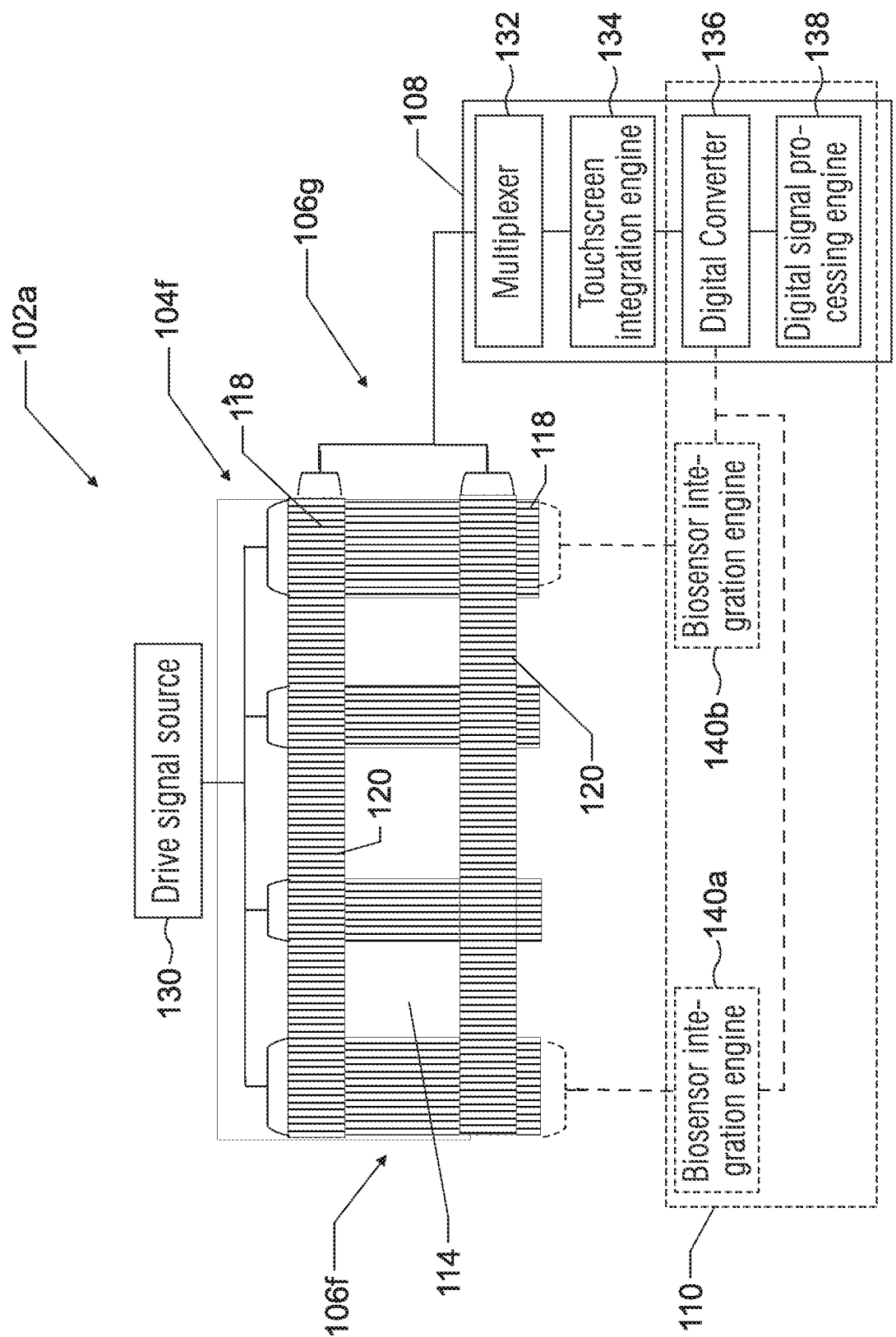
FIG. 5A is a simplified block diagram of a portion of a system to enable a touchscreen with one or more biosensors, in accordance with an embodiment of the present disclosure.

Turning to FIG. 5A, FIG. 5A is a simplified block diagram of a portion of an electronic device 102*b* when touchscreen mode is enabled. Electronic device 102*b* can include touchscreen 104*f*, touchscreen engine 108, biosensor engine 110, and drive signal source 130. Touchscreen 104*f* can include photoconductive material 114, drive lines 118, and sense lines 120. Touchscreen engine 108 can include multiplexer 132, touchscreen integration engine 134, analog to digital converter 136, and digital signal processing engine 138. Biosensor engine 110 can include analog to digital converter 136, digital signal processing engine 138, and a biosensor integration engine 140*a* and 104*b*. Touchscreen 104*f* can include biosensing area 106*f* and 106*g*, drive lines 118, and sense lines 120. In an example, biosensor engine 110 can be coupled to a plurality of drive lines to create biosensing area 106*f* and biosensing area 106*g*.

Drive signal source 130 can be coupled to drive lines 118 and configured to drive a timed pulse on each of drive lines 118. When a user's finger touches the screen of the electronic device (e.g., protective covering 112), the user's finger causes a change in capacitance of the current that flows through drive line 118 and causes a voltage change in sense lines 120 in the area of the user's finger. The pattern of the voltage changes in sense lines 120 can be communicated to touchscreen engine 108. The pattern of the voltage changes in sense lines 120 can be analyzed, for example by touchscreen engine 108, to detect where on protective covering 112 the user's finger touched protective covering 112.

More specifically, in an example, the pattern of the voltage changes in sense lines 120 can be communicated to multiplexer 132. Multiplexer 132 combines the output from sense lines 120 and communicates the combined output to touchscreen integration engine 134. Touchscreen integration engine 134 integrates the output of multiplexer 132 with respect to time to create an output (e.g., output voltage) that is proportional to the input from multiplexer 132 (e.g., input voltage) integrated over time. Touchscreen integration engine 134 communicates the integrated output of multiplexer 132 with respect to time to analog to digital converter 136. Analog to digital converter 136 converts the analog output of touchscreen integration engine 134 to a digital signal and communicates the digital signal to digital signal processing engine 138. Digital signal processing engine 138 analyzes the signal from analog to digital converter 136 to detect where on protective covering 112 the user's finger touched protective covering 112.

Figure 5B:
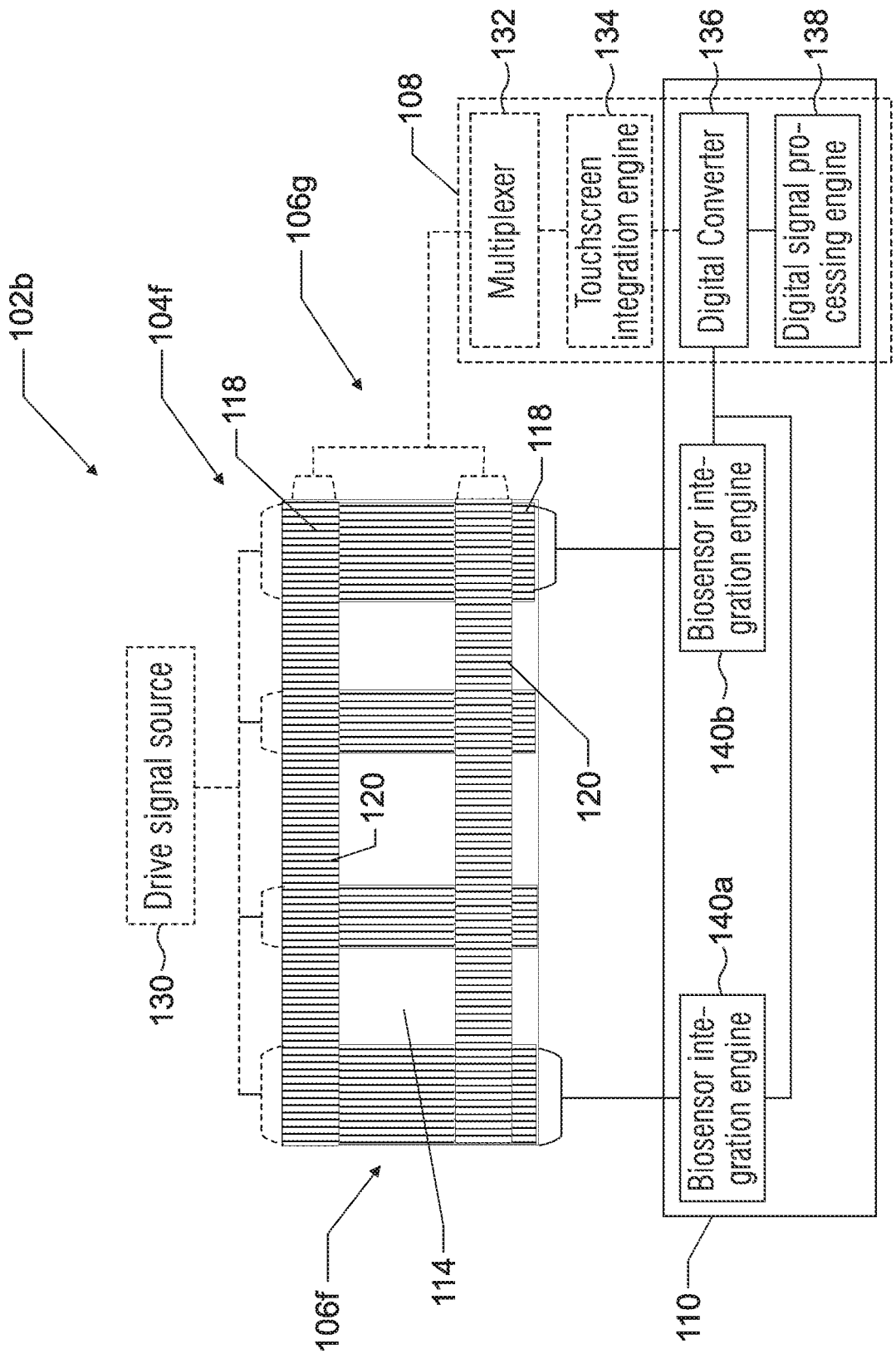
FIG. 5B is a simplified block diagram of a portion of a system to enable a touchscreen with one or more biosensors, in accordance with an embodiment of the present disclosure.

Turning to FIG. 5B, FIG. 5B is a simplified block diagram of a portion of an electronic device 102*b* when biosensing mode is enabled. Electronic device 102*b* can include touchscreen 104*f*, touchscreen engine 108, biosensor engine 110, and drive signal source 130. Touchscreen 104*f* can include biosensing areas 106*f* and 106*g*, photoconductive material 114, drive lines 118, and sense lines 120. Touchscreen engine 108 can include multiplexer 132, touchscreen integration engine 134, analog to digital converter 136, and digital signal processing engine 138. Biosensor engine 110 can include analog to digital converter 136, digital signal processing engine 138, and biosensor integration engines 140*a* and 140*b*. In an example, biosensor engine 110 can be coupled to a plurality of drive lines 118 to create biosensing areas 106*f* and 106*g*.

When a user places their finger in biosensing area 106*f* and/or 106*g*, light from a light source under touchscreen 104*f* can reflect off of the user's finger. The different amounts of light reflecting off the user's finger will interact with photoconductive material 114 and will create a current in drive lines 118 (and sense lines 120) due to the photoconductivity of photoconductive material 114. The current in drive lines 118, due to the photoconductivity of photoconductive material 114, can be analyzed by biosensor engine 110 to create biometric readings of the user.

More specifically, in an example, the current in drive lines 118 due to the photoconductivity of photoconductive material 114 can be communicated to biosensor integration engine 140*a* and/or 140*b*. Biosensor integration engine 140*a* and/or 140*b* integrates the current in drive lines 118 with respect to time to create an output and communicates the output to time to analog to digital converter 136. Analog to digital converter 136 converts the analog output of biosensor integration engine 140*a* and/or 140*b* to a digital signal and communicates the digital signal to digital signal processing engine 138. Digital signal processing engine 138 analyzes the signal from biosensor integration engine 140*a* and/or 140*b* to detect biometric readings of the user.

Figure 6A:
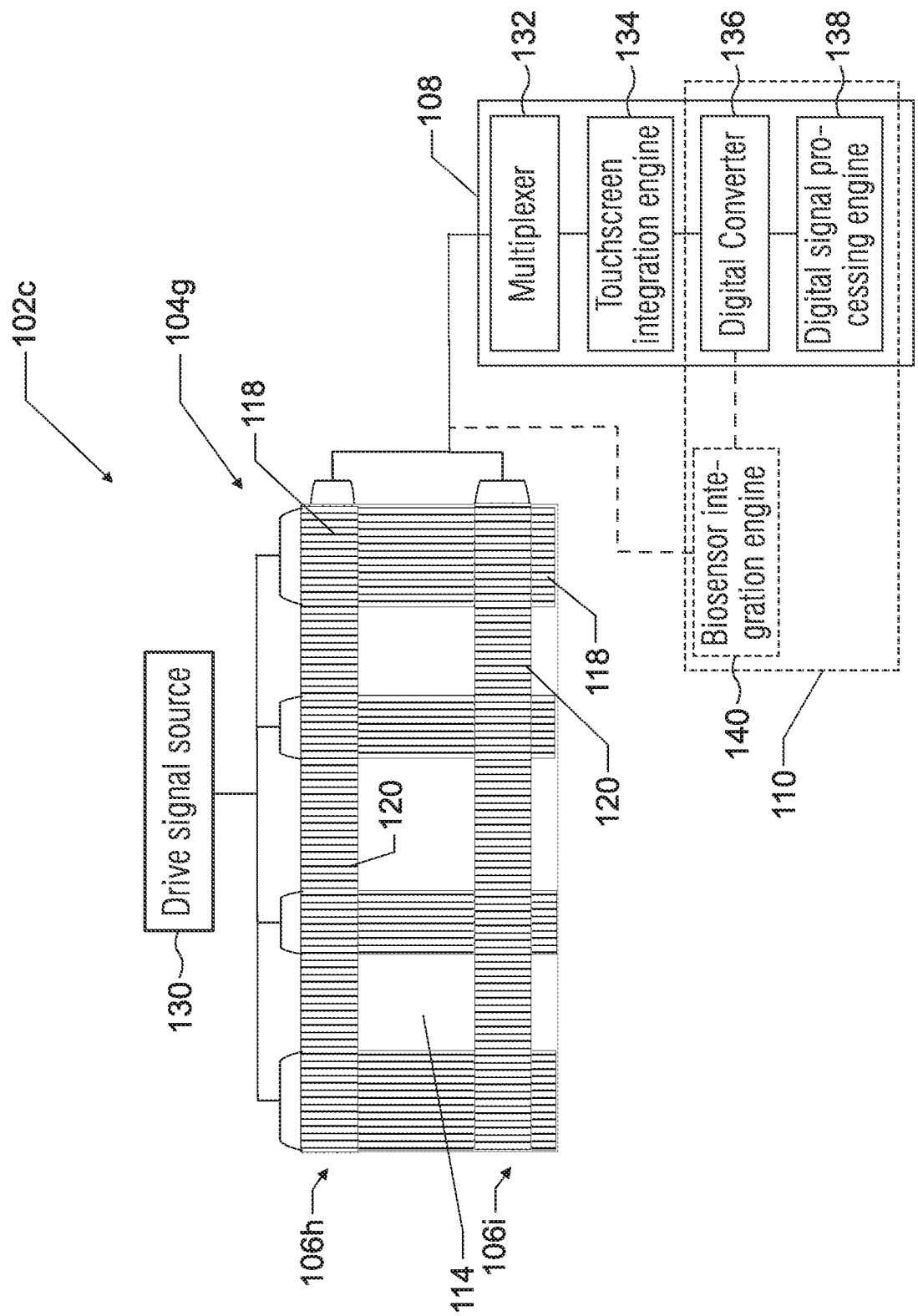
FIG. 6A is a simplified block diagram of a portion of a system to enable a touchscreen with one or more biosensors, in accordance with an embodiment of the present disclosure.

Turning to FIG. 6A, FIG. 6A is a simplified block diagram of a portion of an electronic device 102*c* when touchscreen mode is enabled. Electronic device 102*c* can include touchscreen 104*g*, touchscreen engine 108, biosensor engine 110, and drive signal source 130. Touchscreen 104*g* can include photoconductive material 114, drive lines 118, and sense lines 120. Touchscreen engine 108 can include multiplexer 132, touchscreen integration engine 134, analog to digital converter 136, and digital signal processing engine 138. Biosensor engine 110 can include analog to digital converter 136, digital signal processing engine 138, and biosensor integration engine 140. Touchscreen 104*a* can include biosensing areas 106*h* and 106*i*, drive lines 118, and sense lines 120. In an example, biosensor engine 110 can be coupled to a plurality of sense lines 120 to create biosensing areas 106*h* and 106*i*.

Drive signal source 130 can be coupled to drive lines 118 and configured to drive a timed pulse on each of drive lines 118. When a user's finger touches the screen of the electronic device (e.g., protective covering 112), the finger modifies the voltage in sense lines 120 in the area of the user's finger. The pattern of the voltage changes in sense lines 120 can be communicated to touchscreen engine 108. The pattern of the voltage changes in sense lines 120 can be analyzed, for example by touchscreen engine 108, to detect where on protective covering 112 the user's finger touched protective covering 112.

More specifically, in an example, the pattern of the voltage changes in sense lines 120 can be communicated to multiplexer 132. Multiplexer 132 combines the output from sense lines 120 and communicates the combined output to touchscreen integration engine 134. Touchscreen integration engine 134 integrates the output of multiplexer 132 with respect to time to create an output (e.g., output voltage) that is proportional to the input from multiplexer 132 (e.g., input voltage) integrated over time. Touchscreen integration engine 134 communicates the integrated output of multiplexer 132 with respect to time to analog to digital converter 136. Analog to digital converter 136 converts the analog output of touchscreen integration engine 134 to a digital signal and communicates the digital signal to digital signal processing engine 138. Digital signal processing engine 138 analyzes the signal from analog to digital converter 136 to detect where on protective covering 112 the user's finger touched protective covering 112.

Figure 6B:
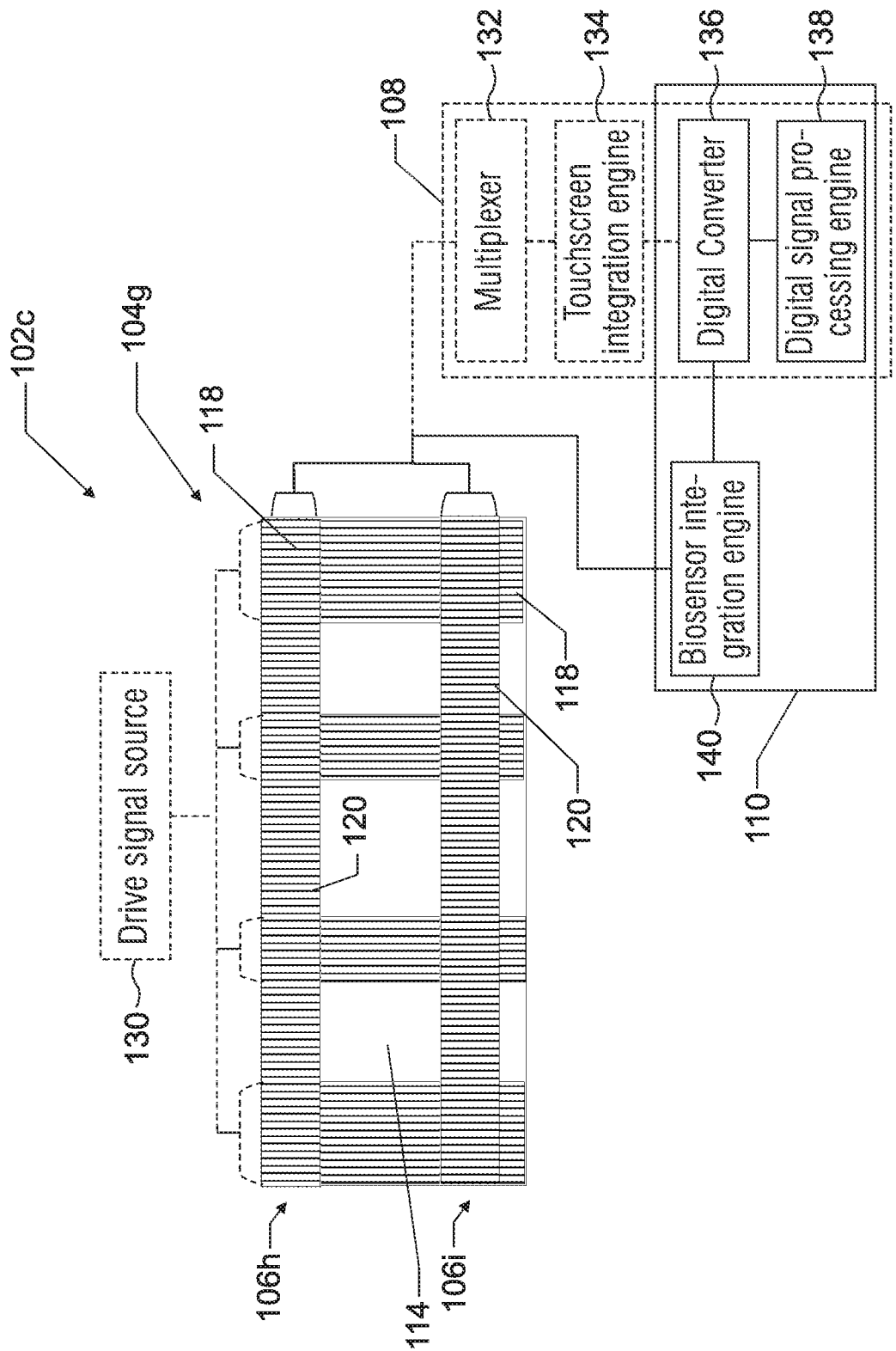
FIG. 6B is a simplified block diagram of a portion of a system to enable a touchscreen with one or more biosensors, in accordance with an embodiment of the present disclosure.

Turning to FIG. 6B, FIG. 6B is a simplified block diagram of a portion of an electronic device 102*c* when biosensing mode is enabled. Electronic device 102*c* can include touchscreen 104*g*, touchscreen engine 108, biosensor engine 110, and drive signal source 130. Touchscreen 104*g* can include photoconductive material 114, drive lines 118, and sense lines 120. Touchscreen engine 108 can include multiplexer 132, touchscreen integration engine 134, analog to digital converter 136, and digital signal processing engine 138. Biosensor engine 110 can include analog to digital converter 136, digital signal processing engine 138, and biosensor integration engine 140. Touchscreen 104g can include biosensing areas 106h and 106i, drive lines 118, and sense lines 120. In an example, biosensor engine 110 can be coupled to a plurality of sense lines 120 to create biosensing areas 106h and 106i.

When a user places their finger in biosensing area 106h and/or 106i, light from a light source under touchscreen 104g can reflect off of the user's finger. The different amounts of light reflecting off the user's finger will interact with photoconductive material 114 and will create a current in sense lines 120 (and drive lines 118) due to the photoconductivity of photoconductive material 114. The current in sense lines 120, due to the photoconductivity of photoconductive material 114, can be analyzed by biosensor engine 110 to create biometric readings of the user.

In an example, the current in sense lines 120 due to the photoconductivity of photoconductive material 114 can be communicated to biosensor integration engine 140. Biosensor integration engine 140 integrates the current in sense lines 120 with respect to time to create an output and communicates the output to time to analog to digital converter 136. Analog to digital converter 136 converts the analog output of biosensor integration engine 140 to a digital signal and communicates the digital signal to digital signal processing engine 138. Digital signal processing engine 138 analyzes the signal from biosensor integration engine 140 to detect biometric readings of the user.

More specifically, while electronic device 110c is in biosensing mode, the light from the light source (e.g., illumination source 116 illustrated in FIGS. 2A and 2B) will pass through photoconductive material 114 and create a current in drive lines 118 and sense lines 120. Also, some of the light from the light source will reflect off of a user's finger (e.g., user's finger 122 illustrated in FIG. 2B) and the reflected light pulses can pass through photoconductive material 114 and create a current in drive lines 118 and sense lines 120. The light that is reflected from the user's finger (an AC component) is directly attributable to variation in blood volume in the skin caused by the pressure pulse of the cardiac cycle. The current on one or more of sense lines 120 can be collected and integrated by biosensor integration engine 140. Analog to digital converter 136 converts the analog output of biosensor integration engine 140 to a digital signal and communicates the digital signal to digital signal processing engine 138. Digital signal processing engine 138 analyzes the signal from biosensor integration engine 140 that will include constant components of light from the light source and reflected pulses of light from the light source reflecting off of the user's finger. The reflected light will be varied due to the change in volume of the arteries and arterioles in the subcutaneous tissue during blood flow. In some examples, biosensor engine 110 can be configured to remove the constant components and process the variable component as the PPG signal. Biosensor integration engine 140 can apply a high pass filter to remove DC component that represents the light from the light source and pass higher frequencies that are caused by the reflected light off of the user's finer and represent the PPG signal. Hence, each cardiac cycle is represented by a PPG wave with a crest and trough. This allows measurement of physiological parameters such as heart rate.

Figure 7A:
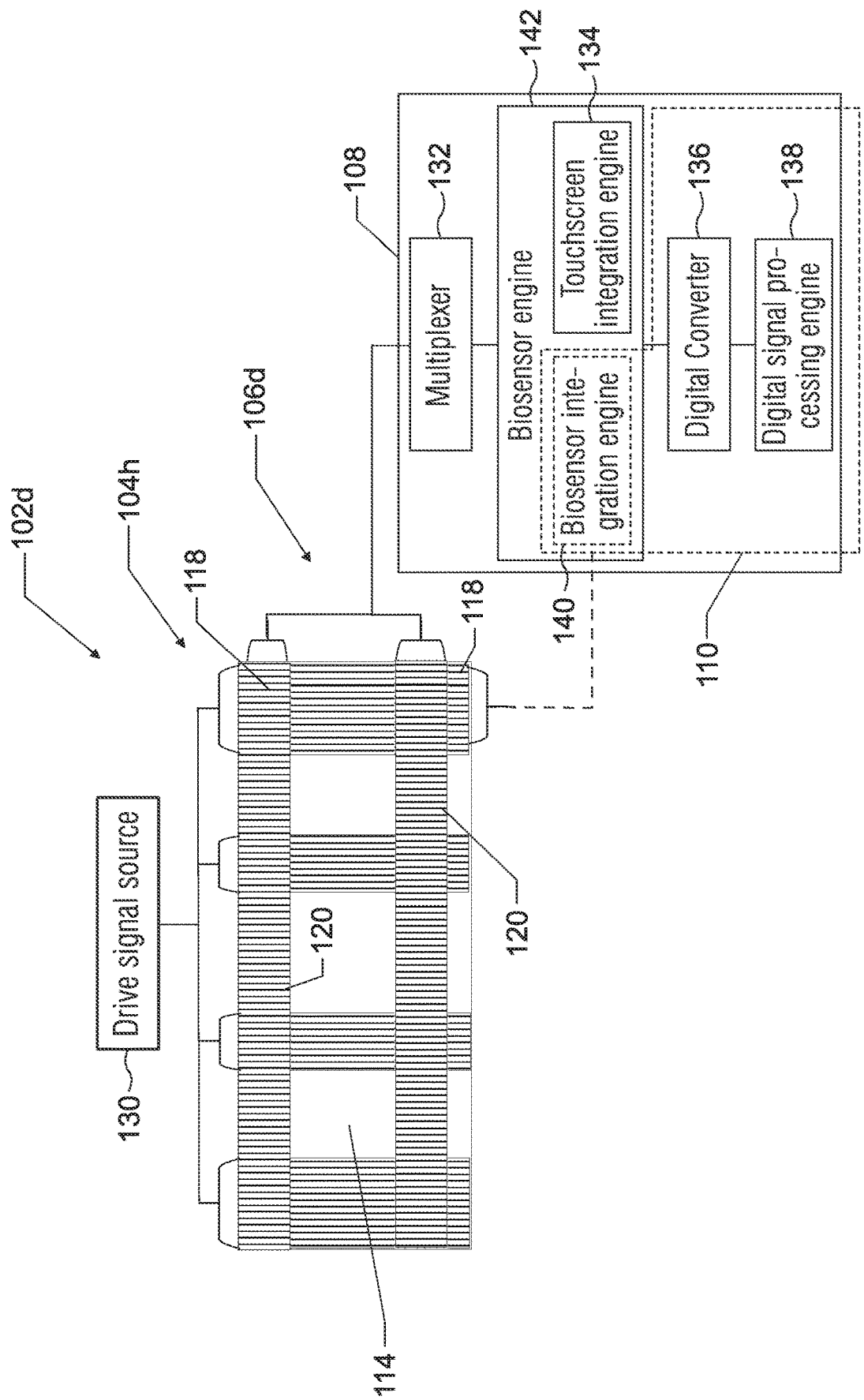
FIG. 7A is a simplified block diagram of a portion of a system to enable a touchscreen with one or more biosensors, in accordance with an embodiment of the present disclosure.

Turning to FIG. 7A, FIG. 7A is a simplified block diagram of a portion of an electronic device 102d when touchscreen mode is enabled. Electronic device 102d can include touchscreen 104h, touchscreen engine 108, biosensor engine 110, and a drive signal source 130. Touchscreen 104h can include photoconductive material 114, drive lines 118, and sense lines 120. Touchscreen engine 108 can include a multiplexer 132, analog to digital converter 136, digital signal processing engine 138, and touchscreen and a biosensor engine 142. Biosensor engine 110 can include analog to digital converter 136, digital signal processing engine 138, and touchscreen and biosensor engine 142. Touchscreen and biosensor engine 142 can include touchscreen integration engine 134 and biosensor integration engine 140. Touchscreen 104a can include biosensing area 106d, drive lines 118, and sense lines 120. In an example, biosensor engine 110 can be coupled to a plurality of drive lines 118 to create biosensing area 106d.

Drive signal source 130 can be coupled to drive lines 118 and configured to drive a timed pulse on each of drive lines 118. When a user's finger touches the screen of the electronic device (e.g., protective covering 112), the current that flows through drive line 118 causes a change in capacitance and a voltage change in sense lines 120 in the area of the user's finger. The pattern of the voltage changes in sense lines 120 can be communicated to touchscreen engine 108. The pattern of the voltage changes in sense lines 120 can be analyzed, for example by touchscreen engine 108 in touchscreen and biosensor engine 142, to detect where on protective covering 112 the user's finger touched protective covering 112.

More specifically, in an example, the pattern of the voltage changes in sense lines 120 can be communicated to multiplexer 132. Multiplexer 132 combines the output from sense lines 120 and communicates the combined output to touchscreen integration engine 134 in touchscreen and biosensor engine 142. Touchscreen integration engine 134 integrates the output of multiplexer 132 with respect to time to create an output (e.g., output voltage) that is proportional to the input from multiplexer 132 (e.g., input voltage) integrated over time. Touchscreen integration engine 134 communicates the integrated output of multiplexer 132 with respect to time to analog to digital converter 136. Analog to digital converter 136 converts the analog output of touchscreen integration engine 134 to a digital signal and communicates the digital signal to digital signal processing engine 138. Digital signal processing engine 138 analyzes the signal from analog to digital converter 136 to detect where on protective covering 112 the user's finger touched protective covering 112.

Figure 7B:
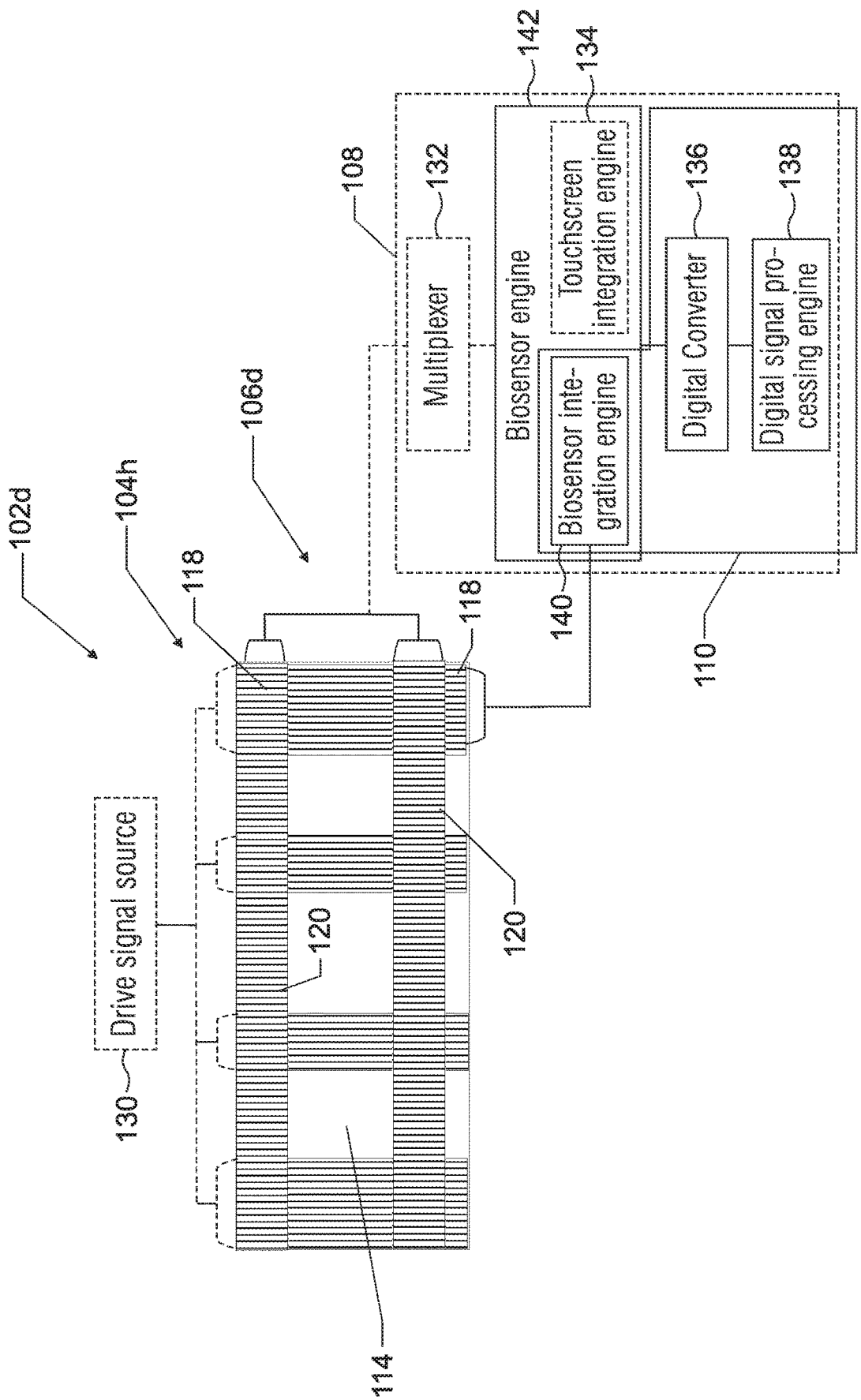
FIG. 7B is a simplified block diagram of a portion of a system to enable a touchscreen with one or more biosensors, in accordance with an embodiment of the present disclosure.

Turning to FIG. 7B, FIG. 7B is a simplified block diagram of a portion of an electronic device 102d when biosensing mode is enabled. Electronic device 102d can include touchscreen 104h, touchscreen engine 108, biosensor engine 110, and a drive signal source 130. Touchscreen 104h can include photoconductive material 114, drive lines 118, and sense lines 120. Touchscreen engine 108 can include a multiplexer 132, analog to digital converter 136, digital signal processing engine 138, and touchscreen and biosensor engine 142. Biosensor engine 110 can include analog to digital converter 136, digital signal processing engine 138, and biosensor engine 142. Touchscreen and biosensor engine 142 can include touchscreen integration engine 134 and biosensor integration engine 140. Touchscreen 104a can include biosensing area 106d, drive lines 118, and sense lines 120. In an example, biosensor engine 110 can be coupled to a plurality of drive lines 118 to create biosensing area 106d.

When a user places their finger in biosensing area 106*d*, light from a light source under touchscreen 104*h* can reflect off of the user's finger. The different amounts of light reflecting off the user's finger will interact with photoconductive material 114 and will create a current in drive lines 118 (and sense lines 120) due to the photoconductivity of photoconductive material 114. The current in drive lines 118, due to the photoconductivity of photoconductive material 114, can be analyzed by biosensor engine 110 in touchscreen and biosensor engine 142 to create biometric readings of the user.

More specifically, in an example, the current in drive lines 118 due to the photoconductivity of photoconductive material 114 can be communicated to biosensor integration engine 140 in touchscreen and biosensor engine 142. Biosensor integration engine 140 integrates the current in drive lines 118 with respect to time to create an output and communicates the output to time to analog to digital converter 136. Analog to digital converter 136 converts the analog output of biosensor integration engine 140 to a digital signal and communicates the digital signal to digital signal processing engine 138. Digital signal processing engine 138 analyzes the signal from biosensor integration engine 140 to detect biometric readings of the user.

Figure 8:
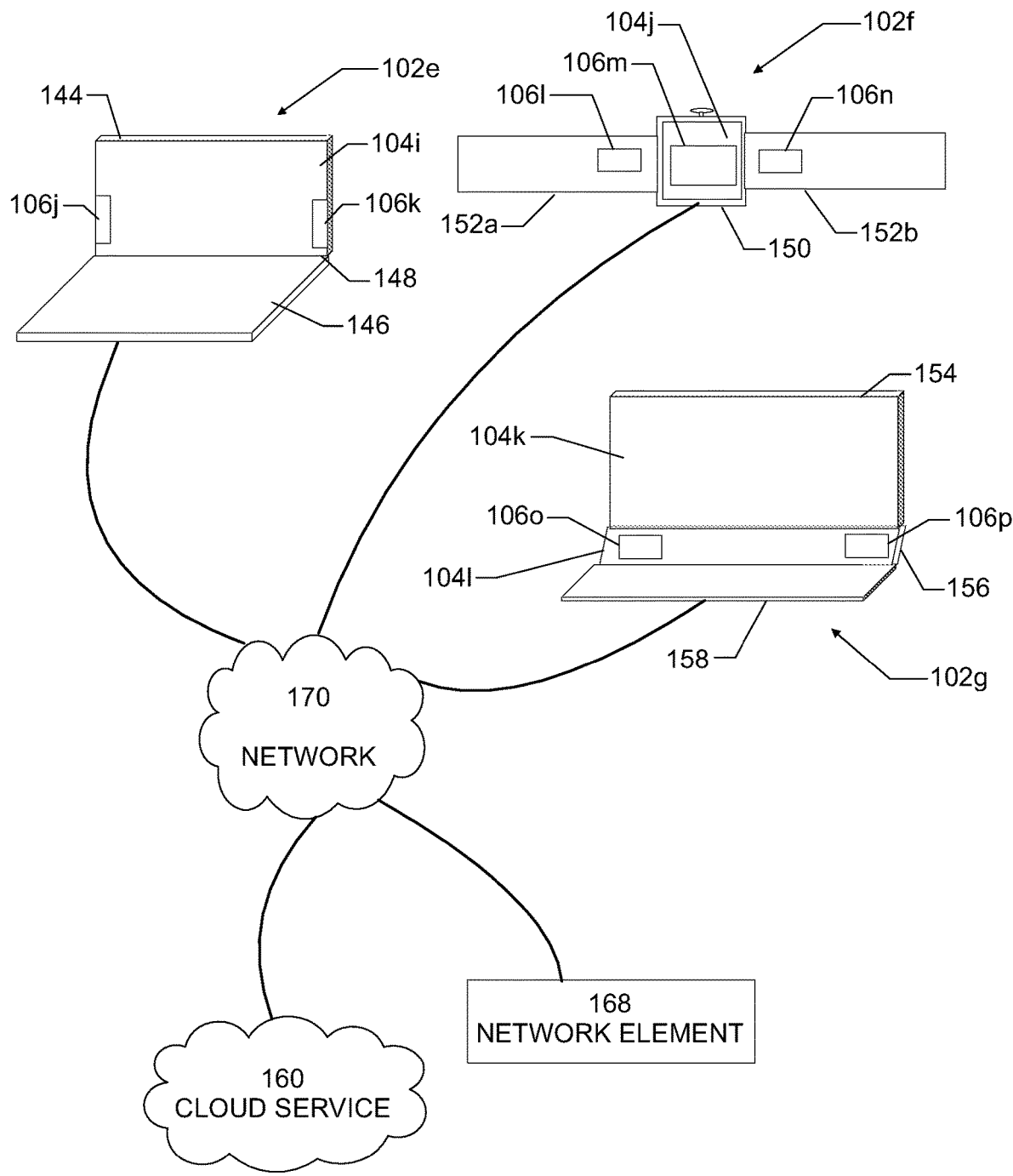
FIG. 8 is a simplified block diagram of a system to enable a touchscreen with one or more biosensors, in accordance with an embodiment of the present disclosure.

Turning to FIG. 8, FIG. 8 is a simplified block diagram of electronic devices 102*e*-102*g* where each of electronic devices 102*e*-102*g* include a touchscreen with one or more biosensors. In an example, electronic device 102*e* may be a laptop, electronic device 102*f* may be a wearable, and electronic device 102*g* may be a dual screen laptop or gaming device. Electronic device 102*e* can include a first housing 144 and a second housing 146. First housing 144 can be rotatably coupled to second housing 146 using a hinge 148. First housing can include a touchscreen 104*i*. Touchscreen 104*i* can include one or more biosensing areas 106*j* and 106*k*. Second housing 146 can include a keyboard.

Electronic device 102*f* can include a main body 150 and wrist straps 152*a* and 152*b*. Main body 150 can include a touchscreen 104*j*. Touchscreen 104*j* can include a biosensing area 106*m*. Also, wrist straps 152*a* and 152*b* can include one or more touchscreens and/or one or more biosensing areas. For example, as illustrated in FIG. 8, wrist strap 152*a* includes biosensing area 106*l* and wrist strap 152*b* includes biosensing area 106*n*. Electronic device 102*g* can include a first display housing 154, a second display housing 156, and a keyboard housing 158. First display housing 154 can include a touchscreen 104*k*. Second display housing can include a touchscreen 104*l*. Touchscreen 104*l* can include one or more biosensing area 106*o* and 106*p*. Keyboard housing 158 can include a keyboard. Each of electronic devices 102*e*-102*g*, and electronic devices 102*a*-102*d*, may be in communication with each other, cloud services 160, and/or network element 162 using network 170. In some examples, one or more of electronic devices 102*e*-102*g*, and electronic devices 102*a*-102*d*, may be standalone devices and not connected to network 170 or another device.

Elements of FIG. 8 may be coupled to one another through one or more interfaces employing any suitable connections (wired or wireless), which provide viable pathways for network (e.g., network 170, etc.) communications. Additionally, any one or more of these elements of FIG. 8 may be combined or removed from the architecture based on particular configuration needs. Electronic devices 102*e*-102*g*, and electronic devices 102*a*-102*d*, may include a configuration capable of transmission control protocol/Internet protocol (TCP/IP) communications for the transmission or reception of packets in a network. Electronic devices 102*e*-102*g*, and electronic devices 102*a*-102*d*, may also operate in conjunction with a user datagram protocol/IP (UDP/IP) or any other suitable protocol where appropriate and based on particular needs.

Turning to the infrastructure of FIG. 8, generally, the system may be implemented in any type or topology of networks. Network 170 represents a series of points or nodes of interconnected communication paths for receiving and transmitting packets of information that propagate through the system. Network 170 offers a communicative interface between nodes, and may be configured as any local area network (LAN), virtual local area network (VLAN), wide area network (WAN), wireless local area network (WLAN), metropolitan area network (MAN), Intranet, Extranet, virtual private network (VPN), and any other appropriate architecture or system that facilitates communications in a network environment, or any suitable combination thereof, including wired and/or wireless communication.

In the system, network traffic, which is inclusive of packets, frames, signals, data, etc., can be sent and received according to any suitable communication messaging protocols. Suitable communication messaging protocols can include a multi-layered scheme such as Open Systems Interconnection (OSI) model, or any derivations or variants thereof (e.g., Transmission Control Protocol/Internet Protocol (TCP/IP), user datagram protocol/IP (UDP/IP)). Messages through the network could be made in accordance with various network protocols, (e.g., Ethernet, Infiniband, OmniPath, etc.). Additionally, radio signal communications over a cellular network may also be provided in the system. Suitable interfaces and infrastructure may be provided to enable communication with the cellular network.

The term "packet" as used herein, refers to a unit of data that can be routed between a source node and a destination node on a packet switched network. A packet includes a source network address and a destination network address. These network addresses can be Internet Protocol (IP) addresses in a TCP/IP messaging protocol. The term "data" as used herein, refers to any type of binary, numeric, voice, video, textual, or script data, or any type of source or object code, or any other suitable information in any appropriate format that may be communicated from one point to another in electronic devices and/or networks. The data may help determine a status of a network element or network. Additionally, messages, requests, responses, and queries are forms of network traffic, and therefore, may comprise packets, frames, signals, data, etc.

Figure 9:
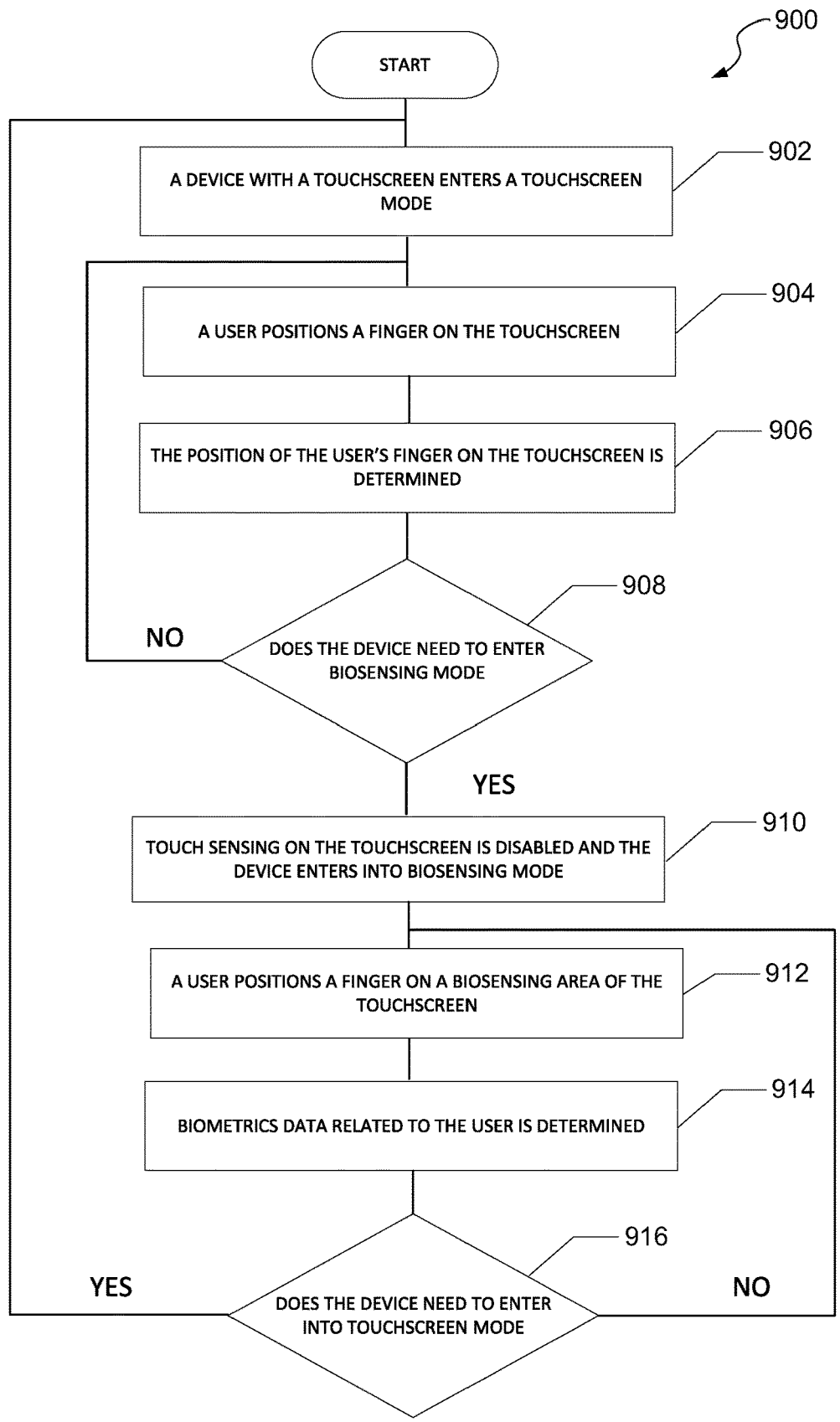
FIG. 9 is a simplified flowchart illustrating potential operations that may be associated with the system in accordance with an embodiment.

Turning to FIG. 9, FIG. 9 is an example flowchart illustrating possible operations of a flow 900 that may be associated with enabling a touchscreen that includes a biosensor, in accordance with an embodiment. In an embodiment, one or more operations of flow 900 may be performed by touchscreen engine 108, biosensor engine 110, touchscreen integration engine 134, biosensor integration engine 140, and touchscreen and biosensor engine 142. At 902, a device with a touchscreen enters a touchscreen mode. At 904, a user positions a finger on the touchscreen. At 906, the position of the user's finger on the touchscreen is determined. At 908, the system determines if the device needs to enter into a biosensing mode. If the device does not need to enter into a biosensing mode, then the system returns to 904 where a user positions a finger on the touchscreen.

If the device does need to enter into a biosensing mode, then touch sensing on the touchscreen is disabled and the device enters into the biosensing mode, as in 910. At 912, a user positions a finger on a biosensing area of the touchscreen. At 914, biometric data related to the user is determined. At 916, the system determines if the device needs to enter into a touchscreen mode. If the device needs to enter into the touchscreen mode, then the device with the touchscreen enters into the touchscreen mode, as in 902. If the device does not need to enter into the touchscreen mode, then the device stays in biosensing mode and the user positions a finger on a biosensing area of the touchscreen, as in 912.

It is also important to note that the operations in the preceding flow diagram (i.e., FIG. 9) illustrates only some of the possible correlating scenarios and patterns that may be executed by, or within, electronic devices 102a-102g. Some of these operations may be deleted or removed where appropriate, or these operations may be modified or changed considerably without departing from the scope of the present disclosure. In addition, a number of these operations have been described as being executed concurrently with, or in parallel to, one or more additional operations. However, the timing of these operations may be altered considerably. The preceding operational flows have been offered for purposes of example and discussion. Substantial flexibility is provided by electronic devices 102a-102g in that any suitable arrangements, chronologies, configurations, and timing mechanisms may be provided without departing from the teachings of the present disclosure.

Figure 10A:
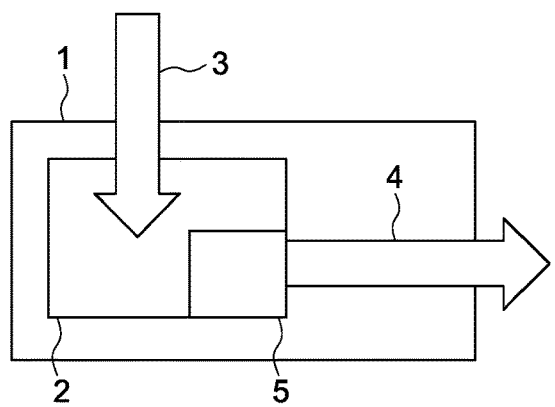
FIG. 10A is a simplified block diagram of an apparatus to determine user related output data of a user, in accordance with an embodiment.

FIG. 10A shows a schematic illustration of an apparatus 1 for determining user related output data of a user. The apparatus 1 comprises a processing circuit 2 and an output interface 5. The processing circuit 2 is configured to generate a control signal indicating a control value for controlling a wavelength of emitted light of a light source and receive user related input data 3 generated based on reflected light reflected by the skin of the user caused by the emitted light having the controlled wavelength emitted by the light source. Further, the processing circuit 2 is configured to determine user related output data 4 of the user based on the user related input data. The output interface 5 is configured to provide the user related output data 4 of the user.

By adapting the wavelength of the emitted light of a light source, the intensity of the reflected light or the properties or the signal to noise ration of the reflected light may be improved and/or adapted to the application.

The processing circuit 2 may generate the control signal so that a light source may be controllable by the control signal to emit light with a desired wavelength. For example, the control value may be represented by a voltage or current of the control signal or may be information carried or contained by the control signal. The control value may be a value triggering the light source to emit light with the desired wavelength.

The emitted light may have a spectral distribution depending on the used light source. The wavelength of the emitted light may be the wavelength of the maximal intensity of the spectral distribution of the emitted light. The wavelength may indicate a color of the emitted light. For example, although the emitted light may comprise portions of light at different wavelengths, the emitted light may be characterized by the wavelength at which the spectrum is at its maximum. For example, light with a first wavelength (with a first color) may have the maximum of the spectrum of the light at the first wavelength and light with a second wavelength (with a second color) may have the maximum of the spectrum of the light at the second wavelength.

The processing circuit 2 may receive an input signal comprising the user related input data from a device (e.g. a touch screen) being connected to the apparatus or being part of the apparatus. The user related input data may be signals containing information on the intensity of reflected light or may comprise information on the user (e.g. PPG related data or ECG related data) determined based on the reflected light. The information on the user may be determined by further processing circuitry (e.g. processor of the touch screen) or may be determined by the processing circuit 2 based on the information on the intensity of reflected light. The user related input data may be biometric input data. Biometric input data may comprise information on a biometric parameter or information usable for determining a biometric parameter (e.g. PPG related data or ECG related data).

The user related output data may be or may contain information on the user (e.g. PPG related data or ECG related data, height or distance) determined based on the user related input data. The user related output data may be biometric data (also called biometrics) or biometric output data containing information on a biometric parameter (e.g. PPG related data or ECG related data) or being based on a biometric parameter (e.g. pulse, blood pressure, blood flow or blood volume).

The processing circuit 2 may be or may comprise a processor (e.g. Central Processing Unit CPU, Digital Signal Processor DSP or microcontroller). For example, the processing circuit 2 may be the CPU of an electronic device or the processor or touch screen controller of a tablet or cell phone.

The output interface 5 may be an output interface or input-output interface of the processing circuit 2 (e.g. for providing an output signal containing the user related output data) or an output device (e.g. a screen, a touch screen or a speaker) for providing the user related output data to the user.

For example, the apparatus 1 may be an apparatus for determining biometric data of a user. The processing circuit 2 may be configured to generate a control signal indicating a (first) control value for controlling a wavelength of emitted light of a light source (e.g. during a first time interval). The processing circuit 2 may be configured to receive biometric input data generated based on reflected light reflected by the skin of the user caused by the emitted light having the controlled (first) wavelength emitted by the light source. Further, the processing circuit 2 may be configured to determine biometric data of the user based on the biometric input data. By adapting the wavelength of the emitted light, a more accurate determination of a biometric parameter of the user may be enabled. The biometric data of the user may be or may comprise photoplethysmogram, PPG, related data and/or electrocardiogram, ECG, related data. The use of PPG may offer a reliable means for monitoring pulse and respiratory rates noninvasively. The electrocardiogram may offer a test that measures the electrical activity of the heartbeat.

The processing circuit 2 may be configured to receive image data of at least a part of the body of the user from a camera. Further, the processing circuit 2 may be configured to determine the control value of the control signal based on the image data. The camera may be an RGB camera.

The processing circuit 2 may be configured to determine a color parameter indicating a skin color of at least the part of the body of the user based on the image data. Further, the processing circuit 2 may be configured to determine the control value of the control signal based on the color parameter. For example, the reflection and/or penetration depth of the emitted light at the user may depend on the color of the skin of the user. The control value for controlling a wavelength of emitted light may be selected depending on the color of the skin of the user, for example, in order to improve the amount of reflected light received from the skin of the user.

The processing circuit 2 may be configured to identify a body part of interest in the image data and determine the color parameter based on the image data of the body part of interest. For example, the processing circuit 2 may use an image recognition algorithm to identify one or more body parts (e.g. hand, face or forehead) in the image of the user. The body part of interest may be the forehead (or a hand) of the user.

Additionally or alternatively, the processing circuit 2 may be configured to identify a plurality of regions of visible skin of the user in the image data and determine the color parameter based on an average of the skin color in the plurality of regions of visible skin of the user. The skin color may vary over the body of the user. For example, the skin color of the hands may be brighter than the skin color of the forehead or some parts of the body of the user may be discolored. By averaging over several parts of the body, the skin color may be determined more reliable.

The processing circuit 2 may be configured to provide the control signal to trigger the light source to emit light with the wavelength being a default wavelength. For example, the light may be emitted with a default wavelength at the beginning and then the wavelength is changed in order to increase the amount of reflected light of interest.

The processing circuit 2 may be configured to change the control value of the control signal so that the light source is triggered to emit light with a different, second wavelength (e.g. during a second time interval). Further, the processing circuit 2 may be configured to receive second biometric input data based on reflected light from the skin of the user caused by the light of the second wavelength emitted by the light source. Additionally, the processing circuit 2 may be configured to change the control value of the control signal so that the light source is triggered to emit light with a different, third wavelength based on a comparison of the second biometric input data with the biometric input data. By varying the wavelength of the emitted light, the amount of reflected light of interest may be increased.

The processing circuit 2 may be configured to determine the control value of the control signal based on a wavelength skin color mapping look-up table. The wavelength skin color mapping look-up table may contain a plurality of control values for a plurality of values of the color parameter. For example, the optimal wavelength of the emitted light for different skin colors may be determined and a corresponding control value causing the light source to emit the light with the desired wavelength may be stored in a look-up table. The apparatus 1 may comprise a memory for storing the wavelength skin color mapping look-up table. The processing circuit 2 may obtain the control value from the look-up table by looking up the control value associated with the skin color being closest to the determined value of the color parameter or may interpolate between two closest values of the color parameter.

Additionally or alternatively, the processing circuit 2 may be configured to determine the control value of the control signal by using a Machine learning, ML, model trained based on a plurality of values of the color parameter and a plurality of corresponding control values.

Additionally or alternatively, the processing circuit 2 may be configured to finetune the control value of the control signal by using stored biometric data morphologies, noise estimation and/or Machine learning, ML, models. This may enable to adapt the wavelength, preferably between the wavelength of green light, 490 nm to 575 nm and the wavelength of red light, 650 nm to 750 nm, even more accurate to the skin color of the user. After finetuning the control value the wavelength skin color mapping look-up table and/or the ML model may be updated.

The processing circuit 2 may be configured to generate the control signal indicating a second control value (e.g. during a second time interval) for controlling a wavelength of emitted light of a light source so that the emitted light comprises a second wavelength different from the first wavelength. Further, the processing circuit 2 may be configured to receive second biometric input data generated based on reflected light reflected by the skin of a second user caused by the emitted light having the controlled second wavelength emitted by the light source (e.g. during a second time interval). Additionally, the processing circuit 2 may be configured to determine second biometric data of the second user based on the second biometric input data (e.g. during a second time interval). For example, a first user with a first skin color may use the apparatus 1 or an electronic device comprising the apparatus 1 during the first time interval and a second user with a second skin color may use the apparatus 1 or an electronic device comprising the apparatus 1 during the second time interval. The wavelength of the emitted light may be adapted to the different users in order to increase the amount of reflected light of interest individually.

The processing circuit 2 may be configured to receive second image data of at least a part of the body of the second user from the camera. Further, the processing circuit 2 may be configured to determine the second control value of the control signal based on the second image data.

The processing circuit 2 may be configured to determine a second color parameter indicating a skin color of at least the part of the body of the second user based on the second image data. Further, the processing circuit 2 may be configured to determine the second control value of the control signal based on the second color parameter.

The apparatus 1 for determining user related output data (e.g. biometric data) of a user may be part of an electronic device or may be an electronic device.

For example, an electronic device for determining biometric data of a user may comprise a touchscreen and an apparatus for determining biometric data of a user as described above or below. The processing circuit 2 may be configured to generate a control signal indicating a control value for controlling a wavelength of emitted light of a light source of the touchscreen. Further, the processing circuit 2 may be configured to receive biometric input data generated by the touchscreen based on reflected light reflected by the skin of the user caused by the emitted light having the controlled wavelength emitted by the light source. The light source of the touchscreen is configured to generate the emitted light with the wavelength based on the control value.

The electronic device may further comprise a camera. The camera may be configured to generate image data of at least a part of the body of the user.

The touchscreen may comprise drive lines, sense lines, a photoconductive material, at least one biosensing area and/or a light source. The light source may emit the light with the controlled wavelength in the biosensing area. The photoconductive material may be graphene.

The light source may be configured to emit light in a biosensing area of the touchscreen and the sense lines may be configured to detect the biometric input data relating to reflected light from the skin of the user caused by the light emitted by the light source and transmit the biometric input data to the processing circuit 2. The drive lines may be disabled during the detection of the biometric input data with the sense lines.

The electronic device may be a computer, a laptop, a tablet or a smart phone, for example.

The apparatus 1 may improve the measurement of biometrics of a user. The apparatus may be implemented to work with a sensor on palm rests, key caps, hinges or the A and C covers of electronic devices, for example.

More details and aspects are mentioned in connection with the embodiments described above or below. The example shown in FIG. 10A may comprise one or more optional additional features corresponding to one or more aspects mentioned in connection with the proposed concept or one or more examples described above (e.g. FIG. 1-9) or below (e.g. FIG. 10B-14).

Some examples relate to a method for determining biometric data of a user. The method comprises generating a control signal indicating a control value for controlling a wavelength of emitted light of a light source and receiving biometric input data generated based on reflected light reflected by the skin of the user caused by the emitted light having the controlled wavelength emitted by the light source. Further the method comprises determining biometric data of the user based on the biometric input data.

More details and aspects are mentioned in connection with the embodiments described above or below.

Some examples relate to a machine-readable storage medium including program code, when executed, to cause a machine to perform one of the methods described above or below. Some examples relate to a having a program code for performing one of the methods described above or below, when the computer program is executed on a computer or processor.

Figure 10B:
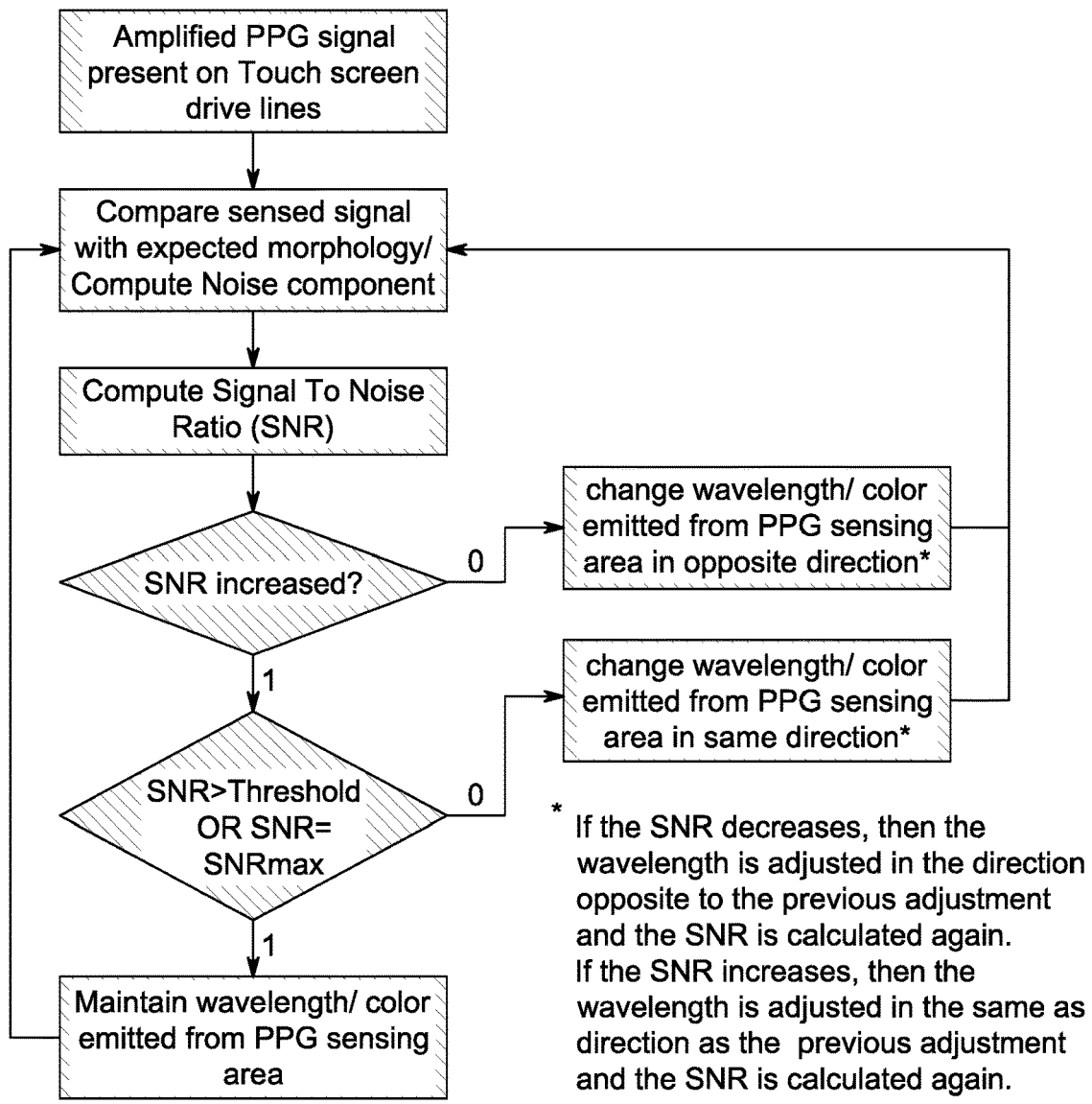
FIG. 10B is a simplified flowchart illustrating the wavelength fine tuning logic, in accordance with an embodiment.

FIG. 10B is a flow chart of a finetuning of the wavelength to improve the signal to noise ratio, SNR, in accordance with an embodiment. As shown in FIG. 10B, first the biometric input data relating to the reflected light 126 from the skin of the user caused by the light 124 emitted of the light source 116 is measured. For example, the preferably amplified PPG signal present on the touchscreen drive lines is measured.

This signal is compared with an expected morphology and/or an computed noise component. Further, the signal to noise ratio, SNR, of the biometric input data is computed and it is determined whether the SNR is increased. If the SNR is not increased, the wavelength (or color) emitted by the light source (e.g. from the PPG sensing area) is changed in the opposite direction as the previous adjustment. If the SNR decreases, then the wavelength is adjusted in the direction opposite to the previous adjustment and the SNR is calculated again (e.g. based on biometric input data caused by light with the adjusted wavelength).

If the SNR is increased, it is determined if the SNR is a maximal SNR (e.g. higher than previously measured SNRs) or is above a predetermined threshold value for the SNR. If the SNR does not the maximal SNR and is not above a threshold value of the SNR, the wavelength of the light emitted by the light source (e.g. from the PPG sensing area) is changed in the same direction as the previous adjustment. If the SNR increases, then the wavelength is adjusted in the same direction as the previous adjustment and the SNR is calculated again (e.g. based on biometric input data caused by light with the adjusted wavelength).

If the SNR is a maximal SNR or is above a threshold value of the SNR, the wavelength of the light emitted by the light source (e.g. from the PPG sensing area) is maintained. The SNR may be calculated again based on biometric input data caused by light with the same wavelength.

More details, optional features and aspects are mentioned in connection with the examples described above or below.

Figure 10C:
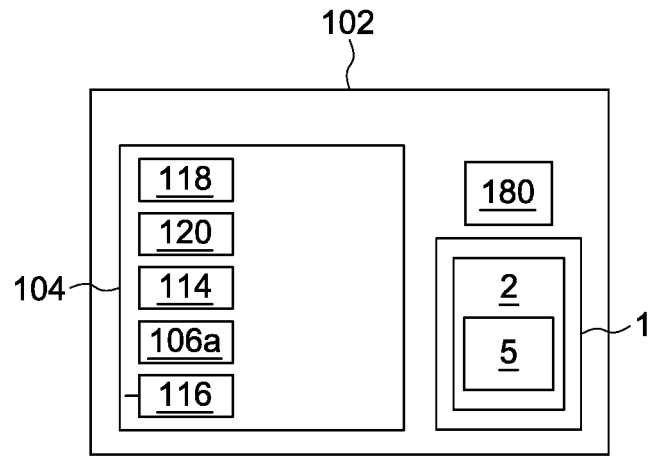
FIG. 10C is a simplified block diagram of an electronic device to determine biometric data of a user, in accordance with an embodiment.

FIG. 10C is shows an electronic device 102 for determining biometric data of a user in accordance with an embodiment of the present disclosure. The electronic device 102 comprises a touchscreen 104. The touchscreen 104 comprises drive lines 118, sense lines 120, a photoconductive material 114, at least one biosensing area 106a and a light source 116. Further, the electronic device 102 comprises a camera 180 and an apparatus for determining biometric data of a user as described above or below (e.g. as described in connection with FIG. 1). The camera 180 is configured to detect the image data containing information on the skin color of the user and transmit the image data to the processing circuit 2. The light source 116 is configured to emit light in a biosensing area 106a on the touchscreen 104 with the wavelength based on the control signal of the processing circuit 2. The sense lines 120 are configured to detect the biometric input data based on the reflected light from the skin of the user caused by the light emitted by the light source 116 and transmit the biometric input data to the processing circuit 2. The drive lines 118 may be disabled during the detection of the biometric input data with the sense lines 120. This electronic device 102 may improve the measurement of biometric data of a user.

The photoconductive material 114 may be graphene. For example, graphene has good photoconductivity.

More details and aspects are mentioned in connection with the embodiments described above or below. The example shown in FIG. 10C may comprise one or more optional additional features corresponding to one or more aspects mentioned in connection with the proposed concept or one or more examples described above (e.g. FIG. 1-10B) or below (e.g. FIG. 11-14).

Some examples may relate to skin pigment based adaptive wavelength touch screen PPG sensing. It may be desired to integrate Biometric sensors in particular PPG (Photoplethysmogram) and ECG (Electrocardiogram) sensors on various PC form factors for intentional sensing. This may be attempted by putting sensors on palm rests, key caps, hinges and the A and C covers. This may result in additional hardware, electronics and device ID modifications. A method and design to use the photo-conductive properties of biased Graphene in touch panels as PPG sensors within the touch screen so that integrated touch controller may be used to process the PPG signal for associated analytics.

For example, the skin transmissivity of light depends on the wavelength. Darker skin offers more resistance to light transmission through the skin to reach blood vessels. Further the optimum wavelength for best transmissivity and penetration with least interference from ambient light is also dependent on the color of the skin. Although, green light is used in PPGLEDs, it is sub optimal for certain skin types.

For example, a method and system are presented, which may generate the optimal wavelength with a screen sensing PPG method and may be considered for future versions of gaming laptops and systems where PPG sensing may be required.

Green light may be used for the PPG LED as it presents the easiest tradeoff for all issues presented due to varying skin color. However, green light has low skin penetration and has high distortion. Red light is also used in some solutions but this results in lower SNR due to ambient interference. Both may be used as a one size fits all method.

It is suggested to automatically adjusts the wavelength of the light to arrive at the best SNR for PPG.

For example, shallower penetrating green illumination results in higher distortion and phase delay with respect to the pressure wave in large arteries, while sampling deeper (red illumination) into the skin minimizes this effect, though at the cost of lower signal quality.

For example, it is proposed to use the integrated camera on a PC to determine the skin color of the user. This information may be used to make an estimate of the optimum wavelength needed and fine tune the wavelength to maximize SNR. Wavelength may be modified by modifying the color emitted by the region of the screen the finger is placed on.

An optimum PPG sensing with best SNR from touch screens on platforms may be achievable. Results with skin color may be optimized due to the inherent challenges presented due to distortion and low SNR by using standard fixed wavelength solutions. The skin color may be kept private within the algorithm on the system.

The feature may be sensed from a touch screen. Visible or measured wavelength changes in the light emitted by the screen in the sensing region of the screen may be used to identify the feature.

Figure 11:
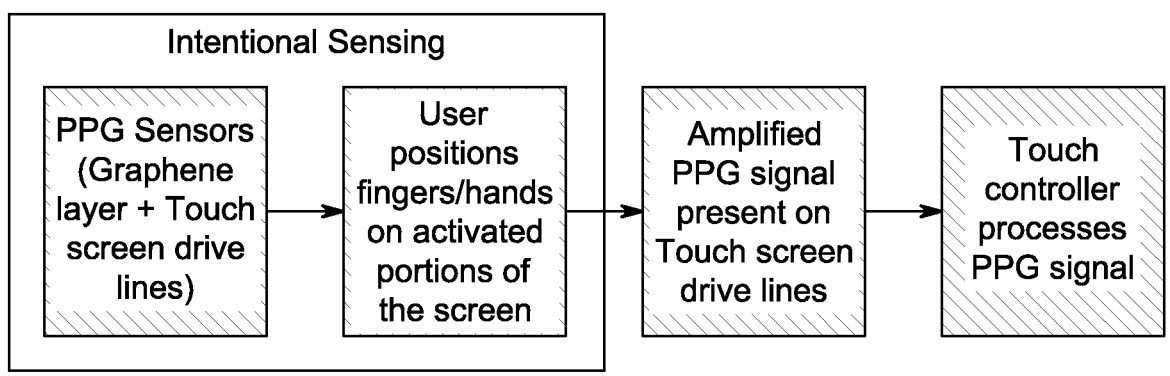
FIG. 11 is a simplified flowchart illustrating existing flow for PPG sensing from touch screens.

FIG. 11 illustrates the flow for PPG sensing using touch screens. The PPG sensing may be performed as described in connection with the examples described above. An intentional sensing is performed by a PPG sensor (e.g. graphene layer and touch screen drive lines) and the user positions his fingers or hands on activated portions of the screen. The PPG signal present on the touch screen drive lines is amplified and the touch controller processes the PPG signal.

Figure 12:
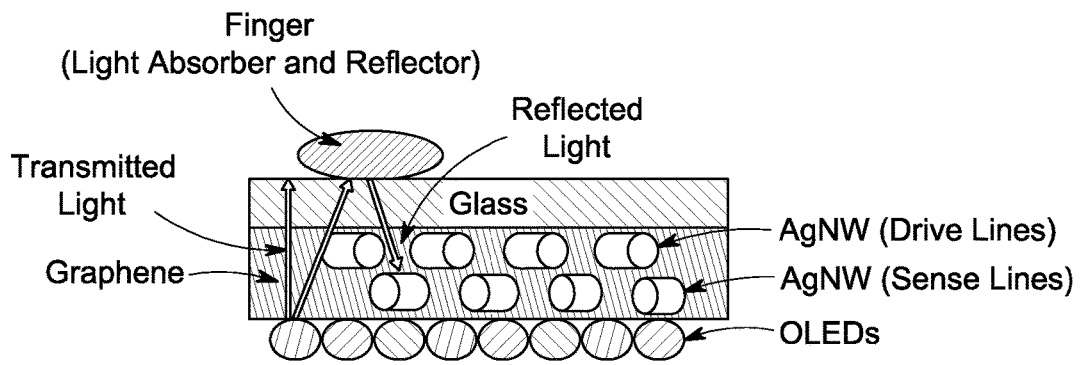
FIG. 12 is a simplified block diagram of light reflection when a finger is placed on a touch panel.

FIG. 12 illustrates the light reflection when a finger is placed on a touch panel that comprises graphene, drive lines and sense lines (e.g. silver nano wires AgNW. The light that is transmitted from the LEDs passes through the touch layer (Graphene+drive+sense lines). When a finger is placed on the glass, part of this light is reflected back towards the touch panel. The transmitted light will create current in the drive and sense lines due to the photoconductivity of the Graphene-metal junctions. The reflected component will also create a similar current component which contains a constant component and a variable component that corresponds to the user's PPG. The photocurrent generated (~nA) will be negligible compared to the drive current (~µA) and hence, in order to sense voltage and/or current changes that correspond to PPG signal, the drive lines during times of sensing may be disabled. This can be controlled by the intentional PPG sensing application. During intentional sensing periods, portions of the screen at the sensing area may be illuminated in pulses. Pulses are used so that the touch screen area directly above the LEDs may be used for sensing PPG. The reflection of these pulses from the user's finger/s are sensed on the drive and/or sense lines, amplified and analyzed by the touch controller to derive the PPG.

Figure 13A:
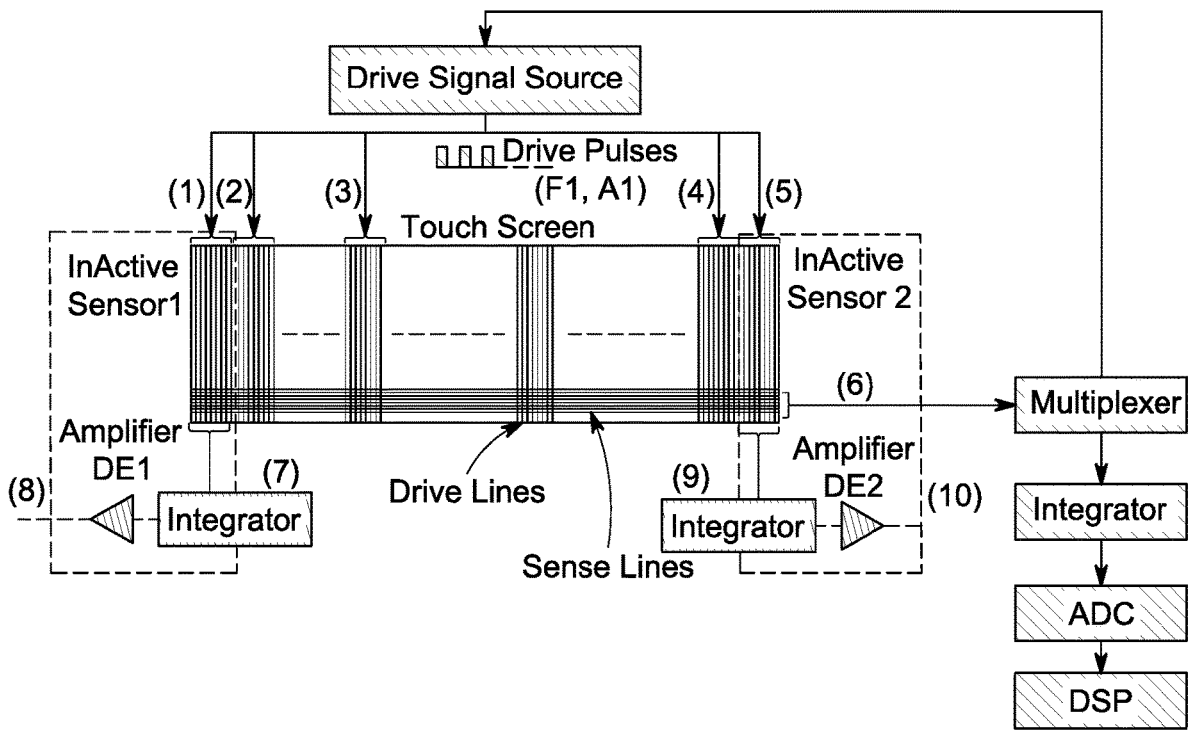
FIG. 13A is a simplified block diagram of a portion of an electronic device to enable a touchscreen with one or more biosensors, for example a touch panel integrated with PPG sensors (inactive), in accordance with an embodiment of the present disclosure.

FIG. 13A illustrates a touch screen with integrated sensors. The touch screen may be implemented similar to the touch screens described in connection with FIGS. 2A-7B and may comprise an apparatus for determining biometric data of a user as described in connection with FIG. 10A. When the PPG sensors (sensor 1 and sensor 2) are inactive (not sensing), the touch screen may work as usual, where, the timed drive signal pulses (e.g. with a frequency F1 and an amplitude A1) are sent along drive lines and the signal on the sense line/s are measured to detect when a finger is placed on the screen. Points 7 to 10 (amplifier 1, amplifier 2 and first and second integrator) may be disabled or inactive as shown in FIG. 13A.

Figure 13B:
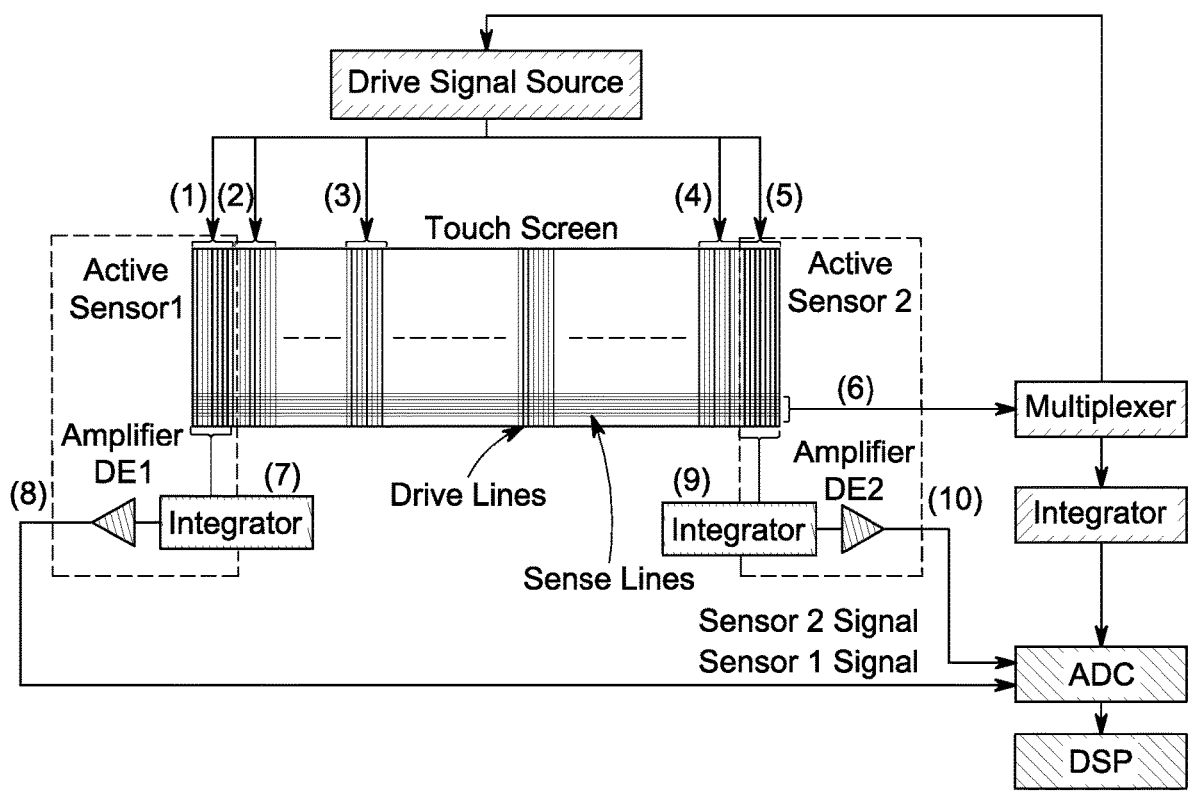
FIG. 13B is a simplified block diagram is a simplified block diagram of a portion of a system to enable a touchscreen with one or more biosensors, for example a touch panel (disabled) integrated with PPG Sensors (active), in accordance with an embodiment of the present disclosure.

When the PPG sensors are activated to measure PPG, the touch drive pulse circuit (drive signal source) may be disabled. This is illustrated in FIG. 13B. Points 1-6 (drive signal supply and sense signal output) will be inactive, while points 7 to 10 (amplifier 1, amplifier 2 and first and second integrator) will be activated to create active sensors that can measure reflected light changes. For example, normal touch functionality may be disabled in order to measure small changes in current due to PPG.

More details, optional features and aspects are mentioned in connection with the examples described above or below.

Figure 14:
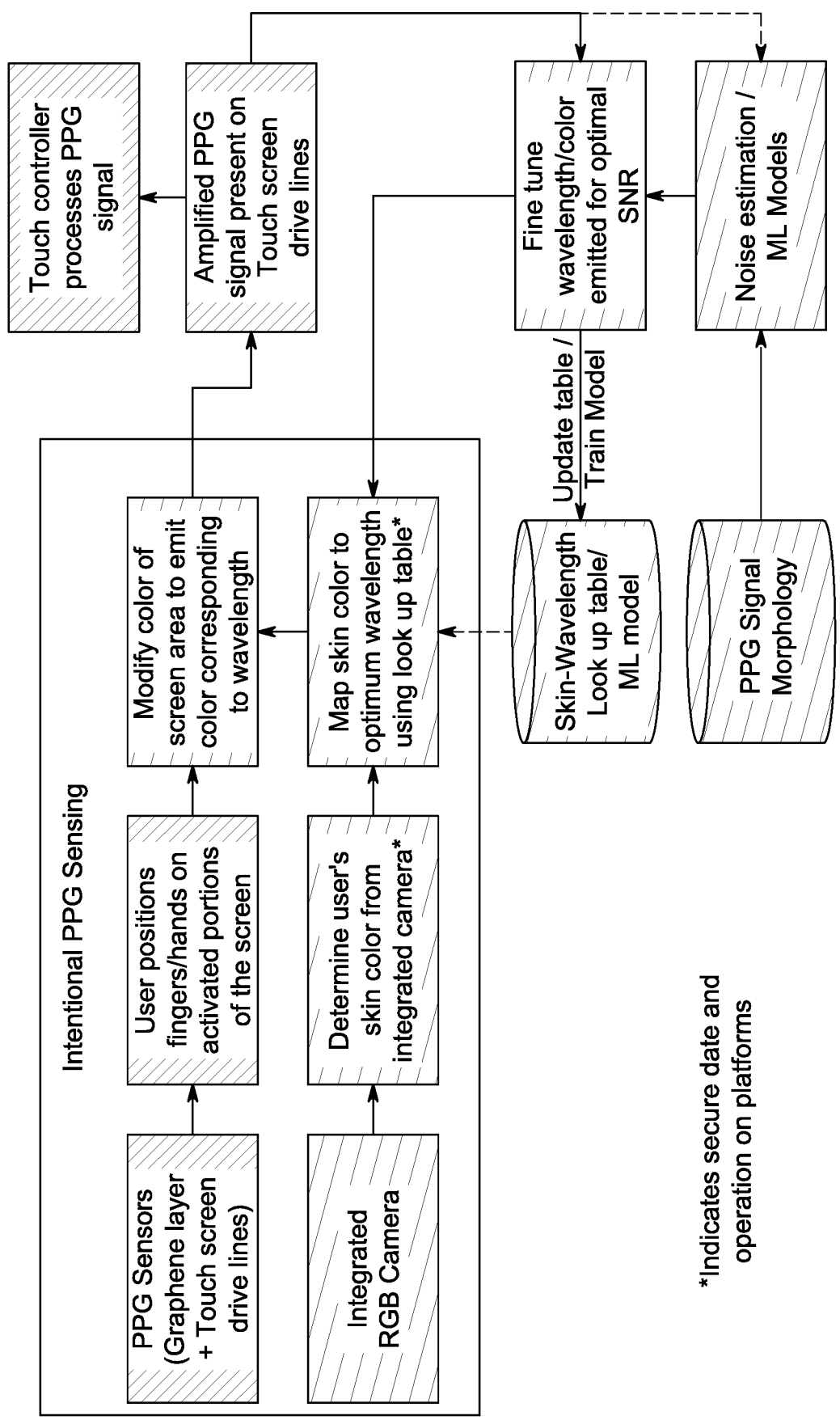
FIG. 14 is a simplified flowchart illustrating PPG sensing with adaptive wavelength for different skin colors.

A proposed device may use the integrated camera to estimate the skin color of the user. This color estimate may be used to determine the closest optimum wavelength (e.g. between green and red light wavelengths) for best PPG SNR. The screen pixels on the active sensing area of the screen are driven to generate a color corresponding to the optimum wavelength for PPG sensing for the user's skin color. The wavelength/screen pixel color to skin color mapping can be stored in a look up table or be generated using an ML model trained with this mapping data. This is illustrated in FIG. 14, where the user's skin color is estimated using the integrated RGB camera, when a user places fingers on the active sensing region of the screen for PPG sensing. This estimate is used to look up the best wavelength for PPG sensing and illuminate the sensing region of the screen with the color that maps to this wavelength.

An intentional PPG sensing is performed by a PPG sensor (e.g. graphene layer and touch screen drive lines) and the user positions his fingers or hands on activated portions of the screen.

Further, an integrated camera takes an image of the user and the user's skin color is determined from the image from the integrated camera. The skin color may be secure data and operation may take place on the platform (not externally). The skin color may be mapped to an optimum wavelength using a look-up table. The look-up table may be secure data and operation may take place on the platform. The color of the screen may be modified to emit color corresponding to the determined wavelength.

Then, the PPG signal present on the touch screen drive lines may be amplified and the touch controller processes the PPG signal.

The look-up table may be a skin-wavelength look-up table. Alternatively or additionally, a ML model may be used.

A fine tuning of the wavelength and/or color may be performed to emit light for optimal SNR. The fine tuning may be performed based on the amplified PPG signal (e.g. FIG. 10B). The look-up table may be updated or the ML model may be trained based on the fine tuning.

The fine tuning may be based on a noise estimation and/or ML models based on a PPG signal morphology database.

The wavelength may be fine-tuned once the optimum wavelength has been determined. This fine tuning may improve the SNR and is done using the stored PPG signal morphologies and noise estimation ML models. This is illustrated in FIG. 10B.

More details and aspects are mentioned in connection with the embodiments described above or below. The example shown in FIGS. 11, 12, 13A, 13B and 14 may comprise one or more optional additional features corresponding to one or more aspects mentioned in connection with the proposed concept or one or more examples described above (e.g. FIG. 1-10C).

Example A1, is an electronic device including a touchscreen, a touchscreen engine, and a biosensor engine. The touchscreen can include drive lines, sense lines, a photoconductive material, and one or more biosensing areas. When a touchscreen mode is activated, the touchscreen engine is configured to couple with the sense lines and determine a place on the touchscreen where a user touched the touchscreen with a finger. When a biosensing mode is activated, the biosensor engine is configured to determine biometrics of the user when the user touches at least one of the one or more biosensing areas.

In Example A2, the subject matter of Example A1 can optionally include where the photoconductive material is graphene.

In Example A3, the subject matter of any one of Examples A1-A2 can optionally include where the biometrics of the user includes photoplethysmogram (PPG) related data.

In Example A4, the subject matter of any one of Examples A1-A3 can optionally include a light source, where light from the light source reflects off of the user's finger and causes a current to flow in a plurality of the drive lines.

In Example A5, the subject matter of any one of Examples A1-A4 can optionally include where the biosensor engine uses the current in the plurality of the drive lines to determine the biometrics of the user.

In Example A6, the subject matter of any one of Examples A1-A5 can optionally include a light source, where light from the light source reflects off of the user's finger and causes a current to flow in a plurality of the sense lines.

In Example A7, the subject matter of any one of Examples A1-A6 can optionally include where the biosensor engine uses the current in the plurality of the sense lines to determine the biometrics of the user.

Example M1 is a method including determine a place on a touchscreen where a user touched the touchscreen, where the touchscreen includes drive lines, sense lines, and photoconductive material, creating a biosensing area on the touchscreen, and determining biometrics of the user when the user touches the biosensing area.

In Example M2, the subject matter of Example M1 can optionally include where the photoconductive material is graphene.

In Example M3, the subject matter of any one of the Examples M1-M2 can optionally include where the biometrics of the user includes photoplethysmogram (PPG) related data.

In Example M4, the subject matter of any one of the Examples M1-M3 can optionally include where the biosensing area is at least partially created when a drive signal source for the touchscreen is disabled.

In Example M5, the subject matter of any one of the Examples M1-M4 can optionally include where light from the light source reflects off of a user's finger and causes a current to flow in at least a portion of the drive lines.

In Example M6, the subject matter of any one of the Examples M1-M5 can optionally include where a biosensor engine uses the current to determine the biometrics of the user.

Example S1 is a system for enabling a touchscreen with a biosensor. The system can include one or more processors, a touchscreen, a touchscreen engine, and a biosensor engine. The touchscreen can include drive lines, sense lines, a photoconductive material, one or more biosensing areas, and a drive signal source. When a touchscreen mode is activated, the drive signal sources is activated and touchscreen engine is configured couple with the sense lines and to cause at least one of the one or more processors to determine a place on the touchscreen where a user touched the touchscreen with a finger. When a biosensing mode is activated, the drive signal source is deactivated and biosensor engine is configured to cause at least one of the one or more processors to determine biometrics of the user when the user touches at least one of the one or more biosensing areas.

In Example S2, the subject matter of Example S1 can optionally include where the photoconductive material is graphene.

In Example S3, the subject matter of any one of the Examples S1-S2 can optionally include where the biometrics of the user includes photoplethysmogram (PPG) related data.

In Example S4, the subject matter of any one of the Examples S1-S3 can optionally include a light source, where light from the light source reflects off of the user's finger and causes a current to flow in a plurality of the drive lines.

In Example S5, the subject matter of any one of the Examples S1-S4 can optionally include where the biosensor engine uses the current in the plurality of the drive lines to determine the biometrics of the user.

In Example S6, the subject matter of any one of the Examples S1-S5 can optionally include a light source, where light from the light source reflects off of the user's finger and causes a current to flow in a plurality of the sense lines.

In Example S7, the subject matter of any one of the Examples S1-S6 can optionally include where the biosensor engine uses the current in the plurality of the sense lines to determine the biometrics of the user.

An example (e.g. example B1) relates to an apparatus to determine biometric data of a user, the apparatus comprising a processing circuit configured to: generate a control signal relating to a control value for controlling a wavelength of emitted light of a light source; receive biometric input data based on reflected light from the skin of the user caused by the light of the wavelength emitted by the light source; and determine biometric data of the user based on the biometric input data; and an output interface configured to provide the biometric data of the user.

Another example (e.g. example B2) relates to a previously described example (e.g. example B1) further comprising the processing circuit being configured to: receive image data of at least a part of the body of the user from a camera; and determine the control value of the control signal based on the image data.

Another example (e.g. example B3) relates to a previously described example (e.g. example B2) further comprising the processing circuit being configured to: determine a color parameter indicating a skin color of at least the part of the body of the user based on the image data; and determine the control value of the control signal based on the color parameter.

Another example (e.g. example B4) relates to a previously described example (e.g. example B3) further comprising the processing circuit being configured to: identify a body part of interest in the image data; and determine the color parameter based on the image data of the body part of interest.

Another example (e.g. example B5) relates to a previously described example (e.g. example B4), wherein the body part of interest being the forehead of the user.

Another example (e.g. example B6) relates to a previously described example (e.g. one of the examples B3-B5) further comprising the processing circuit being configured to: identify a plurality of regions of visible skin of the user in the image data; and determine the color parameter based on an average of the skin color in the plurality of regions of visible skin of the user.

Another example (e.g. example B7) relates to a previously described example (e.g. one of the examples B1-B6) further comprising the processing circuit being configured to generate the control signal relating to the control value triggering the wavelength based on a default wavelength.

Another example (e.g. example B8) relates to a previously described example (e.g. one of the examples B1-B7) further comprising the processing circuit being configured to: change the control value of the control signal so that the light source is triggered to emit light with a different, second wavelength; receive second biometric input data based on reflected light from the skin of the user caused by the light of the second wavelength emitted by the light source; and change the control value of the control signal so that the light source is triggered to emit light with a different, third wavelength based on a comparison of the second biometric input data with the biometric input data.

Another example (e.g. example B9) relates to a previously described example (e.g. one of the examples B1-B8) further comprising the processing circuit being configured to determine the control value of the control signal by using a wavelength skin color mapping look-up table containing a plurality of color parameters and a plurality of corresponding control values.

Another example (e.g. example B10) relates to a previously described example (e.g. one of the examples B1-B9) further comprising the processing circuit being configured to determine the control value of the control signal by using a Machine learning, ML, model trained with a wavelength skin color mapping look-up table containing a plurality of color parameters and a plurality of corresponding control values.

Another example (e.g. example B11) relates to a previously described example (e.g. one of the examples B1-B10) further comprising the processing circuit being configured to finetune the control value of the control signal by using stored biometric data morphologies, noise estimation and/or Machine learning, ML, models.

Another example (e.g. example B12) relates to a previously described example (e.g. one of the examples B1-B11), wherein the biometric data of the user comprises photoplethysmogram, PPG, related data or electrocardiogram, ECG, related data.

An example (e.g. example B13) relates to an electronic device to determine biometric data of a user comprising: a touchscreen, wherein the touchscreen comprises: drive lines, sense lines, a photoconductive material, at least one biosensing area, and a light source; a camera; and the apparatus according to a previously described example (e.g. one of the examples B1-B12), wherein the camera is configured to generate the image data, wherein the light source is configured to emit light in a biosensing area on the touchscreen with the wavelength based on the control signal of the processing circuit, wherein the sense lines are configured to detect the biometric input data relating to reflected light from the skin of the user caused by the light emitted by the light source and transmit the biometric input data to the processing circuit, wherein the drive lines are disabled during the detection of the biometric input data with the sense lines.

Another example (e.g. example B14) relates to a previously described example (e.g. example B13), wherein the photoconductive material is graphene.

Although the present disclosure has been described in detail with reference to particular arrangements and configurations, these example configurations and arrangements may be changed significantly without departing from the scope of the present disclosure. Moreover, certain components may be combined, separated, eliminated, or added based on particular needs and implementations. Additionally, although electronic devices 102a-102g have been illustrated with reference to particular elements and operations that facilitate the communication process, these elements and operations may be replaced by any suitable architecture, protocols, and/or processes that achieve the intended functionality of electronic devices 102a-102g.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) of 35 U.S.C. section 112 as it exists on the date of the filing hereof unless the words "means for" or "step for" are specifically used in the particular claims; and (b) does not intend, by any statement in the specification, to limit this disclosure in any way that is not otherwise reflected in the appended claims.

What is claimed is:

1. An apparatus for determining biometric data of a user, the apparatus comprising:
    a processing circuit configured to:
        receive image data of at least a part of a body of the user from a camera;
        determine a color parameter indicating a skin color of at least the part of the body of the user based on the image data;
        generate a control signal indicating a control value for controlling a wavelength of emitted light of a light source based on a wavelength skin color mapping look-up table, wherein the wavelength skin color mapping look-up table contains a plurality of control values for a plurality of values of the color parameter;
        receive biometric input data generated based on reflected light reflected by the skin of the user caused by the emitted light having the controlled wavelength emitted by the light source; and
        determine biometric data of the user based on the biometric input data; and
    an output interface configured to provide the biometric data of the user.

2. The apparatus according to claim 1, wherein the processing circuit is configured to:
    identify a body part of interest in the image data; and
    determine the color parameter based on the image data of the body part of interest.

3. The apparatus according to claim 2, wherein the body part of interest is the forehead of the user.

4. The apparatus according to claim 1, wherein the processing circuit is configured to:
    identify a plurality of regions of visible skin of the user in the image data; and
    determine the color parameter based on an average of the skin color in the plurality of regions of visible skin of the user.

5. The apparatus according to claim 1, wherein the processing circuit is configured to provide the control signal to trigger the light source to emit light with the wavelength being a default wavelength.

6. The apparatus according to claim 1, wherein the processing circuit is configured to:
change the control value of the control signal so that the light source is triggered to emit light with a different, second wavelength;
receive second biometric input data based on reflected light from the skin of the user caused by the light of the second wavelength emitted by the light source; and
change the control value of the control signal so that the light source is triggered to emit light with a different, third wavelength based on a comparison of the second biometric input data with the biometric input data.

7. The apparatus according to claim 1, wherein the processing circuit is configured to determine the control value of the control signal by using a Machine learning, ML, model trained based on a plurality of values of the color parameter and a plurality of corresponding control values.

8. The apparatus according to claim 1, wherein the processing circuit is configured to tune the control value of the control signal by using stored biometric data morphologies, noise estimation and/or Machine learning, ML, models.

9. The apparatus according to claim 1, wherein the biometric data of the user comprises at least one of photoplethysmogram, PPG, data or electrocardiogram, ECG, data.

10. The apparatus according to claim 1, wherein the processing circuit is configured to:
generate the control signal indicating a second control value for controlling a wavelength of emitted light of a light source so that the emitted light comprises a second wavelength different from the first wavelength;
receive second biometric input data generated based on reflected light reflected by the skin of a second user caused by the emitted light having the controlled second wavelength emitted by the light source; and
determine second biometric data of the second user based on the second biometric input data.

11. The apparatus according to claim 10, wherein the processing circuit is configured to:
receive second image data of at least a part of the body of the second user from the camera; and
determine the second control value of the control signal based on the second image data.

12. The apparatus according to claim 11, wherein the processing circuit is configured to:
determine a second color parameter indicating a skin color of at least the part of the body of the second user based on the second image data; and
determine the second control value of the control signal based on the second color parameter.

13. An electronic device for determining biometric data of a user comprising:
a touchscreen; and
an apparatus for determining the biometric data of a user, the apparatus comprising:
a processing circuit configured to:
receive image data of at least a part of a body of the user from a camera;
determine a color parameter indicating a skin color of at least the part of the body of the user based on the image data;
generate a control signal indicating a control value for controlling a wavelength of emitted light of a light source of the touchscreen based on a wavelength skin color mapping look-up table, wherein the wavelength skin color mapping look-up table contains a plurality of control values for a plurality of values of the color parameter;
receive biometric input data generated by the touchscreen based on reflected light reflected by the skin of the user caused by the emitted light having the controlled wavelength emitted by the light source; and
determine biometric data of the user based on the biometric input data; and
an output interface configured to provide the biometric data of the user.

14. The electronic device according to claim 13, further comprising the camera, wherein the camera is configured to generate the image data of the at least a part of the body of the user, wherein the image data represents the biometric input data.

15. The electronic device according to claim 13, wherein the touchscreen comprises:
drive lines;
sense lines;
a photoconductive material;
at least one biosensing area; and
a light source.

16. The electronic device according to claim 15, wherein the photoconductive material is graphene.

17. The electronic device according to claim 15, wherein the light source is configured to emit light in a biosensing area of the touchscreen,
wherein the sense lines are configured to detect the biometric input data relating to reflected light from the skin of the user caused by the light emitted by the light source and transmit the biometric input data to the processing circuit, wherein the drive lines are disabled during the detection of the biometric input data with the sense lines.

18. An apparatus for determining user related output data of a user, the apparatus comprising:
a processing circuit configured to:
receive image data of at least a part of a body of the user from a camera;
determine a color parameter indicating a skin color of at least the part of the body of the user based on the image data;
generate a control signal indicating a control value for controlling a wavelength of emitted light of a light source based on a wavelength skin color mapping look-up table, wherein the wavelength skin color mapping look-up table contains a plurality of control values for a plurality of values of the color parameter;
receive user related input data generated based on reflected light reflected by the skin of the user caused by the emitted light having the controlled wavelength emitted by the light source; and
determine user related output data of the user based on the user related input data; and
an output interface configured to provide the user related output data of the user.

19. A method for determining biometric data of a user, the method comprising:
receiving image data of at least a part of a body of the user from a camera;
determining a color parameter indicating a skin color of at least the part of the body of the user based on the image data;

generating a control signal indicating a control value for controlling a wavelength of emitted light of a light source based on a wavelength skin color mapping look-up table, wherein the wavelength skin color mapping look-up table contains a plurality of control values for a plurality of values of the color parameter;

receiving biometric input data generated based on reflected light reflected by the skin of the user caused by the emitted light having the controlled wavelength emitted by the light source; and determining biometric data of the user based on the biometric input data.

* * * * *